US011123315B2

(12) United States Patent
Birbara et al.

(10) Patent No.: US 11,123,315 B2
(45) Date of Patent: *Sep. 21, 2021

(54) TOPICAL COMPOSITIONS FOR PAIN RELIEF, MANUFACTURE AND USE

(71) Applicant: PROPELLA THERAPEUTICS INC., Pittsboro, NC (US)

(72) Inventors: Philip J. Birbara, West Hartford, CT (US); Daniel Bucks, Millbrae, CA (US)

(73) Assignee: Propella Therapeutics, Inc., Pittsboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/745,093

(22) Filed: Jan. 16, 2020

(65) Prior Publication Data

US 2020/0323800 A1 Oct. 15, 2020

Related U.S. Application Data

(60) Continuation of application No. 16/243,317, filed on Jan. 9, 2019, now Pat. No. 10,583,100, which is a continuation of application No. 15/939,445, filed on Mar. 29, 2018, now Pat. No. 10,206,892, which is a division of application No. 14/687,566, filed on Apr. 15, 2015, now Pat. No. 9,956,190.

(60) Provisional application No. 61/979,905, filed on Apr. 15, 2014.

(51) Int. Cl.

| *A61K 31/165* | (2006.01) |
| *A61K 9/06* | (2006.01) |
| *A61K 9/08* | (2006.01) |
| *A61K 31/00* | (2006.01) |
| *A61K 31/045* | (2006.01) |
| *A61K 31/05* | (2006.01) |
| *A61K 31/125* | (2006.01) |
| *A61K 31/618* | (2006.01) |
| *A61K 31/728* | (2006.01) |
| *A61K 45/06* | (2006.01) |
| *A61K 47/26* | (2006.01) |
| *A61K 47/36* | (2006.01) |
| *A61K 47/42* | (2017.01) |
| *A61K 47/44* | (2017.01) |
| *A61K 47/10* | (2017.01) |
| *A61K 9/00* | (2006.01) |

(52) U.S. Cl.
CPC .......... *A61K 31/165* (2013.01); *A61K 9/0014* (2013.01); *A61K 9/06* (2013.01); *A61K 9/08* (2013.01); *A61K 31/00* (2013.01); *A61K 31/045* (2013.01); *A61K 31/05* (2013.01); *A61K 31/125* (2013.01); *A61K 31/618* (2013.01); *A61K 31/728* (2013.01); *A61K 45/06* (2013.01); *A61K 47/10* (2013.01); *A61K 47/26* (2013.01); *A61K 47/36* (2013.01); *A61K 47/42* (2013.01); *A61K 47/44* (2013.01)

(58) Field of Classification Search
CPC ....... A61K 31/165; A61K 31/618; A61K 9/00
See application file for complete search history.

(56) References Cited

U.S. PATENT DOCUMENTS

| 4,424,205 | A | 1/1984 | LaHann et al. |
| 4,486,450 | A | 12/1984 | Bernstein |
| 4,997,853 | A | 3/1991 | Bernstein |
| 5,134,166 | A | 7/1992 | Bernstein |
| 5,178,879 | A | 1/1993 | Adekunle et al. |
| 5,560,910 | A | 10/1996 | Crandall |
| 5,910,512 | A | 6/1999 | Conant |
| 5,962,532 | A | 10/1999 | Campbell et al. |
| 6,239,180 | B1 | 5/2001 | Robbins |
| 6,348,501 | B1 | 2/2002 | Holt et al. |
| 6,573,302 | B1 | 6/2003 | Holt et al. |
| 6,593,370 | B2 | 7/2003 | Tamura et al. |
| 6,689,399 | B1 | 2/2004 | Dickson |
| 7,282,224 | B1 | 10/2007 | Roederer |
| 7,632,519 | B2 | 12/2009 | Jamieson et al. |
| 7,771,760 | B2 | 8/2010 | Jamieson et al. |
| 7,943,166 | B2 | 5/2011 | Muhammad et al. |
| 7,943,666 | B2 | 5/2011 | Singh et al. |
| 8,435,565 | B2 | 5/2013 | Royer |
| 8,637,569 | B2 | 1/2014 | Birbara |
| 8,703,741 | B2 | 4/2014 | Meyer |
| 8,802,736 | B2 | 8/2014 | Bucks et al. |
| 8,889,659 | B2 | 11/2014 | Bucks et al. |
| 10,085,956 | B2 | 10/2018 | Birbara et al. |
| 2005/0090557 | A1 | 4/2005 | Muhammad et al. |
| 2006/0100272 | A1 | 5/2006 | Maniar |
| 2006/0148903 | A1 | 7/2006 | Burch et al. |

(Continued)

FOREIGN PATENT DOCUMENTS

| EP | 1 000 618 | 5/2000 |
| EP | 2 316 420 | 2/2014 |

(Continued)

OTHER PUBLICATIONS

Abstract of Hautkappe et al., "Review of the Effectiveness of Capsaicin for Painful Cutaneous Disorders and Neural Dysfunction," *Clinical Journal Pain*, pp. 97-106, vol. 14, Issue 2, Jun. 1998.

(Continued)

*Primary Examiner* — Kamal A Saeed

(74) *Attorney, Agent, or Firm* — Nixon & Vanderhye P.C.

(57) ABSTRACT

The present invention relates to TRPV1 selective agonist compositions including a capsaicinoid, a surfactant and an extended release agent, and to methods of manufacture and methods of providing pain relief as well as treating a variety of disorders with such compositions.

1 Claim, 1 Drawing Sheet

(56) References Cited

U.S. PATENT DOCUMENTS

| | | |
|---|---|---|
| 2008/0153780 A1 | 6/2008 | Meyer |
| 2008/0262091 A1 | 10/2008 | Burch et al. |
| 2011/0311592 A1 | 12/2011 | Birbara |
| 2012/0115808 A1 | 5/2012 | Della Valle et al. |
| 2012/0289597 A1 | 11/2012 | Farber |
| 2016/0106690 A1 | 4/2016 | Bucks et al. |

FOREIGN PATENT DOCUMENTS

| | | |
|---|---|---|
| JP | 2006-522832 | 10/2006 |
| JP | 2007-297460 | 11/2007 |
| JP | 2008-525505 | 7/2008 |
| JP | 2012-102097 | 5/2012 |
| WO | WO 2004/091521 | 10/2004 |
| WO | WO 2006/058140 | 6/2006 |
| WO | WO 2013/036961 | 3/2013 |
| WO | WO 2014/075084 | 5/2014 |

OTHER PUBLICATIONS

Abstract of Watson et al. "A Randomized Vehicle-Controlled Trial of Topical Capsaicin in the Treatment of Postherpetic Neuralgia," *Clinical Therapeutics*, pp. 510-526, vol. 15, No. 3, May-Jun. 1993.
Anand et al., "Topical Capsaicin for Pain Management: Therapeutic Potential and Mechanisms of Action of the New High-Concentration Capsaicin 8% Patch," *British Journal of Anesthesia*, pp. 490-502, vol. 107, No. 4, Aug. 2011.
Bernstein et al., "Topical Capsaicin Treatment of Chronic Postherpetic Neuralgia," *Journal of the American Academy of Dermatology*, pp. 265-270, vol. 21, No. 2, Pt. 1, Aug. 1989.
Conquer HA Joint Comfort Rub. (listed for sale on conquerha.com between Jun. 18, 2011 and Sep. 2, 2011, Wayback Machine by Internet Archive: https://web.archive.org/web/*/http://www.conquerha.com:80/jointcomfort.php). (Year: 2011).
Farwick, et al., "Low Molecular Weight Hyaluronic Acid: Its Effects on Epidermal Gene Expression and Skin Ageing," *International Journal for Applied Science (SOFW Journal)*, vol. 134, Nov. 2008.
Fuchs et al., "Secondary hyperalgesia persists in capsaicin desensitized skin," *Pain* pp. 141-149, vol. 84, Iss. 2-3, Feb. 2000.
Hans Ole Klingenberg: "48 International Pharmaceutical Industry Hyaluronic Acid—Creation of Slow-release Formulations for", Oct. 1, 2013, XP055541903, Retrieved from the Internet: URL: https://pdfs.semanticscholar.org/64ca/lf6ccl6ff5e8c19a8704a589bff1924675c5.pdf.
Heyneman et al., "Oral versus Topical NSAIDs in Rheumatic Diseases: A Comparison," *Drugs*, pp. 555-574, vol. 60, No. 3, Sep. 2000.
Kadir et al., "α-Bisabolol, a Possible Safe Penetration Enhancer for Dermal and Transdermal Therapeutics," *International Journal of Pharmaceutics*, pp. 87-94, vol. 70, 1991.
MB Brown et al.: "Hyaluronic acid: a unique topical vehicle for the localized delivery of drugs to the skin", Jeadv. Journal of the European Academy of Dermatology and Venereology., vol. 19, No. 3, May 1, 2005, pp. 308-318, XP055541928, NL, ISSN: 0926-9959, DOI: 10.1111/j.1468-3083.2004.01180.x.
Peikert et al., "Topical 0.025% Capsaicin in Chronic Post-Herpetic Neuralgia: Efficacy, Predictors of Response and Long-Term Course," *Journal of Neurology*, pp. 452-456, vol. 238, No. 8, Dec. 1991.
Robbins et al., "Treatment of Intractable Pain with Topical Large-Dose Capsaicin: Preliminary Report," *Anesth. Analg.* pp. 579-583, vol. 86, 1998.
International Preliminary Report on Patentability issued in PCT/US2015/025957 dated Oct. 18, 2016.
International Searching Authority, "International Search Report," issued in connection with International Patent Application No. PCT/US2015/025957, dated Aug. 4, 2015 (5 pages).
International Searching Authority, "Written Opinion," issued in connection with International Patent Application No. PCT/US2015/025957, dated Aug. 4, 2015 (7 pages).
Office Action issued in AU Appln. No. 2015247649 dated Oct. 3, 2018.
Office Action issued in CA Appln. No. 2,945,818 dated Mar. 26, 2019.
Office Action issued in EP Appln. No. 15 719 102.4 dated Jan. 24, 2019.
Office Action issued in IN Appln. No. 201617036701 dated Apr. 29, 2019 (translation included).
Office Action issued in JP Appln. No. 2016-562863 dated May 24, 2018 (w/ translation).

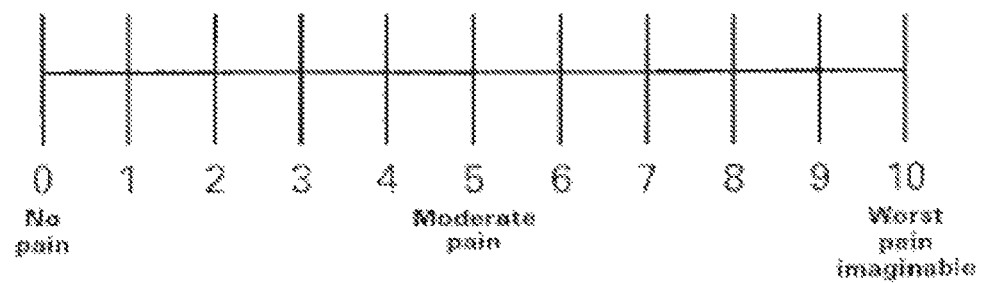

TOPICAL COMPOSITIONS FOR PAIN RELIEF, MANUFACTURE AND USE

This application is a continuation of U.S. application Ser. No. 16/243,317 filed Jan. 9, 2019, which is a continuation of U.S. application Ser. No. 15/939,445 filed Mar. 29, 2018 (now U.S. Pat. No. 10,206,892), which is a divisional of U.S. application Ser. No. 14/687,566 filed Apr. 15, 2015 (now U.S. Pat. No. 9,956,190), which claims priority to U.S. Provisional Application No. 61/979,905 filed Apr. 15, 2014, the entire contents of each of which are incorporated herein by reference.

FIELD OF THE INVENTION

The present invention relates to compositions of transient receptor potential vanilloid 1 (TRPV1) selective agonists such as capsaicin, methods of manufacture and methods of providing pain relief, as well as methods of treating a variety of medical conditions.

BACKGROUND OF THE INVENTION

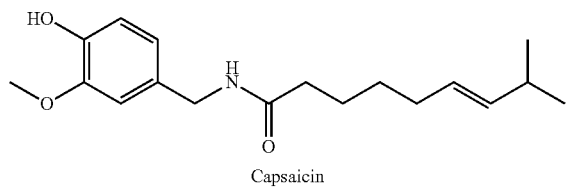 [SMILES: COc1cc(CNC(=O)CCCC/C=C/C(C)C)ccc1O]

Capsaicin

Capsaicin is the main capsaicinoid in capsicum plants including chili peppers. Capsaicin is a solid at room temperatures with a melting point of 60-62° C. It is a pungent substance that has long been used for the relief of pain because of its selective action on the small diameter afferent nerve fibers (C fibers and A-delta fibers) that are believed to signal pain. From studies in animals, capsaicin appears to trigger C fiber membrane depolarization by opening cation channels permeable to calcium and sodium.

Capsaicin has been reported to work by depleting a compound called Substance P, which is a neuropeptide that functions as a neurotransmitter and promotes pain perception, from the nerve terminal fibers. However, capsaicin also can elicit erythema and/or an intense burning or stinging sensation upon application. The intense burning or stinging can be intolerable for some. Additionally, it may take more than a day or two for effectuating actual pain relief, and for the intense burning to stop. Following the initial period of intense burning pain that may be accompanied by erythema, topical capsaicin application causes insensitivity to pain elicited by a variety of noxious stimuli or disease states. In theory, neurons shut down after they've been stimulated by capsaicin, so the burning and other unrelated sensations—including pain—cease. The results from studies testing the low concentrations of capsaicin present in most over-the-counter products (0.075 percent or less) have not been impressive. Many people are bothered by the burning sensation, so they don't stick with the treatment. Current over-the-counter capsaicin products are not effective for many people. High-dose capsaicin patches have been developed, but they require local or regional anesthesia to address the burning and stinging, and therefore are only appropriate for treatment for severe chronic pain under the supervision of a physician.

Because of the ability of capsaicin to desensitize nociceptors in peripheral tissues, their potential analgesic effects have been assessed in various clinical trials. However, since the application of capsaicin itself frequently causes burning pain and hyperalgesia apart from the neuropathic pain being treated, patient compliance has been poor and the dropout rates during clinical trials have typically exceeded fifty percent. The most frequently encountered adverse effect with capsaicin is burning pain at the site of application, particularly in the first week of application. This can make it impossible to blind trials and can lead to dropout rates ranging from 33 to 67% (Watson C P et al. "*A randomized vehicle-controlled trial of topical capsaicin in the treatment of postherpetic neuralgia.*" Clinical Therapeutics. 15.3 (1993):510-26.) Another factor in compliance is the time delay before therapeutic effect is observed. Daily topical applications for at least a week or two may be required.

Many individuals discontinue the prolonged treatment of topical capsaicin prior to the anticipated analgesic effects of capsaicin due to the intense stinging and burning pain. It was reported that 26 out of 39 (66.7%) patients suffering from post-herpetic neuralgia did not tolerate the treatment of a 0.025% capsaicin preparation (Zostrix, Gen Derm, USA). With a 0.075% preparation (Zostrix-HP, Gen Derm, USA), 5 out of 16 (31.3%) and 45 out of 74 (60.8%) patients with post-herpetic neuralgia did not tolerate the long term topical treatment. (Peikert, A. et al., *Topical 0.025% capsaicin in chronic post-herpetic neuralgia: efficacy, predictors of response and long-term course, J. Neurol.* 238:452-456, 1991; Watanabe, A. et al., *Efficacy of capsaicin ointment (Zostrix) in the treatment of herpetic pain and postherpetic neuralgia, Pain Clinic* 15:709-713, 1994; Bernstein J. E. et al., *Topical capsaicin treatment of chronic postherpetic neuralgia, J. Am. Acad. Dermatol.* 21: 265-270, 1989; and Watson C P. N. et al., *A randomized vehicle-controlled trial of topical capsaicin in the treatment of postherpetic neuralgia, Clin. Ther.* 15:510-526, 1993.)

The spontaneous burning pain and hyperalgesia are believed to be due to intense activation and temporary sensitization of the peripheral nociceptors at the site of capsaicin application. This activation and sensitization occurs prior to the desensitization phase and is a barrier to topical capsaicin use because the burning pain produced compromises patient's tolerability of treatment.

Capsaicin is believed to relieve pain by causing a localized degradation of the C neuron endings. The activity of capsaicin results from its binding to, and activating, an ion channel called vanilloid receptor 1, or VR1. Under normal circumstances, when the VR1 ion channel is activated, it opens for a short time, causing the C neurons to transmit a pain signal toward the brain. When capsaicin binds to, and activates VR1, it causes a series of events within the cell that degrade the pain-sensing endings, or terminals of the C neuron, thereby preventing the neuron from transmitting pain signals.

In 1997, a research team led by David Julius of University of California, San Francisco showed that capsaicin selectively binds to a protein known as TRPV1 that resides on the membranes of pain and heat sensing neurons. TRPV1 is a heat activated calcium channel, which opens between 37 and 45° C. (98.6 and 113° F., respectively). When capsaicin binds to TRPV1, it causes the channel to open below 37° C. (normal human body temperature), which is why capsaicin is linked to the sensation of heat. Prolonged activation of these neurons by capsaicin depletes presynaptic substance P, one of the body's neurotransmitters for pain and heat. Neurons that do not contain TRPV1 are unaffected. The result appears to be that the chemical mimics a burning sensation; the nerves are overwhelmed by the influx, and are unable to report pain for an extended period of time. With chronic exposure to capsaicin, neurons are depleted of neurotransmitters, leading to reduction in sensation of pain and blockade of neurogenic inflammation. If capsaicin is removed, the neurons recover.

Although the analgesic effect of capsaicin was thought to be due to a depletion in the pain-causing substance P, recent evidence suggests a process of "defunctionalization" of nociceptor fibers is responsible for its analgesic effect. (Anand P, Bley K. *Topical capsaicin for pain management: therapeutic potential and mechanisms of action of the new high-concentration capsaicin 8% patch. Br J. Anaesth.* 2011; 107(4):490-502.)

Humans have long been exposed to dietary sources of capsaicin-containing spices and to topical preparations used for a variety of medical indications. This vast experience has not revealed significant or lasting adverse effects of capsaicin exposure. The recent determination of potential therapeutic effects of capsaicin on unmyelinated sensory afferent nerve fibers requires diligent consideration of this compound for further pharmaceutical development.

Capsaicin is currently marketed for topical administration in the form of over-the-counter, low dose, non-sterile creams and patches, which tend to be poorly absorbed. There are more than thirty brands of creams and patches, including CapZasin™ (Chattem) and Zostrix™ (Rodlen Laboratories). These over-the-counter preparations can be purchased widely without a prescription and are used topically by consumers to relieve pain with variable and often inadequate results in conditions such as osteoarthritis, shingles (herpes zoster), psoriasis and diabetic neuropathy.

In addition to relieving pain, capsaicin triggers the body to increase blood flow to promote natural healing on the skin surface and within the epidermal layers. This is especially important for healing injuries and environmental damage from pollution, sun and winter weather. Capsaicin is also a powerful anti-microbial that destroys bacteria in clogged skin pores and hair follicles.

Topical capsaicin has been used in skin and scalp care products that target a variety of conditions including acne, dermatitis, eczema, psoriasis and even dandruff. Capsaicin can stop itching when topically applied. Known in the medical world as pruritus, itching is both a symptom and a cause of many skin ailments. The more a person itches, the more they scratch and the worse their condition becomes. Unfortunately, many skin and scalp conditions cause itching that leads to a chronic cycle of sick skin. From bug bites to eczema, the key to fast healing is to stop the itch so the condition can heal naturally, and capsaicin is a known natural substance that can effectively do this.

Capsaicin mediated effects include: (i) activation of nociceptors in peripheral tissues; (ii) eventual desensitization of peripheral nociceptors to one or more stimulus modalities: (iii) cellular degeneration of sensitive A-delta and C-fiber afferents; (iv) activation of neuronal proteases; (v) blockage of axonal transport; and (vi) the decrease of the absolute number of nociceptive fibers without affecting the number of non-nociceptive fibers.

The use of capsaicin is known for the treatment of a number of pain disorders. Accordingly, topical preparations of capsaicin find use as a topical therapy for a variety of skin disorders that involve pain and itching, such as postherpetic neuralgia, diabetic neuropathy, pruritus, psoriasis, cluster headache, postmastectomy pain syndrome, rhinopathy, oral mucositis, cutaneous allergy, detrusor hyperreflexia, loin pain/hematuria syndrome, neck pain, amputation stump pain, reflex sympathetic dystrophy, pain due to skin tumor and arthritis including rheumatoid arthritis, osteoarthritis, diabetic neuropathy, psoriasis, pruritus (itching), cluster headache, post-surgical pain, oral pain, and pain caused by injury, amongst others. (Martin Hautkappe et al., *Review of the Effectiveness of Capsaicin for Painful Cutaneous Disorders and Neural Dysfunction, Clin. J. Pain.* 14:97-106, 1998).

Capsaicin is used in topical ointments and creams to relieve minor aches and pains of muscles and joints. Capsaicin is also available in large adhesive bandages that can be applied to the back. Concentrations of capsaicin are typically between 0.025 wt. % and 0.075 wt. %.

One approach toward minimizing adverse effects and accelerating the rate of analgesia has been to topically apply a higher capsaicin concentration as practiced by the Qutenza® (capsaicin) 8% patch under regional anesthesia. Application of the Qutenza® (capsaicin) 8% patch provides for sustained analgesia lasting 1 to 8 weeks in cases of complex regional pain syndrome and neuropathic pain (Robbins et al. *Treatment of intractable pain with topical large-dose capsaicin: preliminary report. Anesth. Analg.* 1998; 86:579-583). When topical local anesthetics were applied with 1% topical capsaicin, no alteration in pain produced by the capsaicin was observed in healthy subjects indicating that this co-treatment approach was not sufficient to block the pain induced by capsaicin (Fuchs et al., *Secondary hyperalgesia persists in capsaicin desensitized skin. Pain* 2000; 84: 141.)

Topical Analgesics

The primary use of a topical analgesic is to relieve the pain such as that associated with arthritis as well as muscle aches and pains caused by sports injuries or physical work. One benefit of topical pain relievers is that they can be applied directly to the site of the pain, so there is minimal systemic distribution of the pain reliever throughout the body. This localized application and associated action minimizes the potential for systemic side effects. In addition, the pain relieving action of topical analgesics is faster than most oral forms because it is applied directly onto the painful area whereas oral analgesics need to be digested, absorbed in the gastrointestinal tract, survive first-pass metabolism in the liver and then be transported throughout the body.

Ingredients possessing analgesic and other desirable therapeutic properties include eugenol, thymol and several essential oils. Eugenol, a component of clove oil and some essential oils, has analgesic, anti-inflammatory, and antibacterial effects. Eugenol can also be mixed with other pain reducing products to increase the pain relief.

Thymol is an essential oil found in several species of thyme and oregano plants that contains significant antibacterial, antifungal, antiseptic, analgesic and antioxidant properties.

NSAIDs

NSAIDs decrease pain, inflammation, and fever by blocking cyclooxygenase (COX) enzymes. Understanding of the pharmacology of NSAIDs continues to evolve, but it is now thought that most NSAIDs block three different COX isoenzymes, known as COX-1, COX-2, and COX-3. COX-1 protects the lining of the stomach from acid. COX-2 is found in joint and muscle, and mediates effects on pain and inflammation. By blocking COX-2, NSAIDs reduce pain compared to placebo in patients with arthritis, low back pain, minor injuries, and soft tissue rheumatism. However, NSAIDs that also block the COX-1 enzyme (also called "nonselective NSAIDs") can cause gastrointestinal bleeding.

Clinical trials have demonstrated that topical NSAIDs have a better safety profile than oral NSAIDs. Adverse effects secondary to topical NSAID use occurs in about 10 to 15% of patients and are primarily cutaneous (rash and pruritus where the topical NSAID was applied). Gastrointestinal adverse drug reactions are rare with topical NSAIDs, compared with a 15% incidence reported for oral NSAIDs. Hayneman, C. et al. *Oral versus topical NSAIDs in rheumatic diseases: a comparison, Drugs*, pgs. 555-74, September, 2000.

Several topical formulations combine NSAIDS, primarily diclofenac salts, with capsaicin. TABLE 1 below contains a listing of several of these formulations.

TABLE 1

Topical Formulations Containing Capsaicin & Diclofenac Salts

| ITEM NO. | TRADE NAME | ACTIVE INGREDIENTS | COMPANY |
|---|---|---|---|
| 1 | Topac Fast | Gel; Topical; Capsaicin 0.025%; Diclofenac Sodium 1%; Menthol 5%; Methyl Salicylate 5% | Abbott |
| 2 | Voveran Thermagel | Gel; Topical; Capsaicin 0.025%; Diclofenac Sodium 1%; Menthol 5%; Methyl Salicylate 5% | Novartis |
| 3 | Xidol Gel | Gel; Topical; Capsaicin 0.025%; Diclofenac Diethylamine 1.16%; Linseed Oil 3%; Menthol 5%; Methyl Salicylate 10% | Dewcare Concept |
| 4 | Diclomax Power | Gel; Topical; Capsaicin 0.025%; Diclofenac Diethylamine 1.16%; Linseed Oil 3%; Menthol 5%; Methyl Salicylate 10% | Torrent Pharmaceuticals |
| 5 | Divexx Gel | Gel; topical; Capsaicin 0.022%; Diclofenac Sodium 1%; Menthol 5%; Methyl Salicylate 10% | Zuventus Healthcare |

Gellert Joint Cream has a capsaicin concentration of 0.17% and contains 74% water. The current aqueous capsaicin formulations are limited by relatively low capsaicin concentrations.

U.S. Pat. No. 4,424,205 discloses a variety of hydroxyphenylacetamides having analgesic and anti-irritant properties.

U.S. Pat. No. 4,486,450 discloses a method and composition of treating psoriatic skin in which capsaicin is applied topically to the psoriatic skin in a pharmaceutically acceptable carrier wherein capsaicin is present in therapeutically acceptable concentrations of between about 0.01 and about 1 percent by weight. Subsequent exposure of the treated psoriatic skin to ultraviolet light in small doses aids treatment.

U.S. Pat. No. 4,997,853 discloses a method and composition for treating superficial pain syndromes, which incorporates capsaicin into a pharmaceutically acceptable carrier, and adding to this composition a local anesthetic such as lidocaine or benzocaine. The composition containing the anesthetic is then applied to the site of the pain. A variation on the treatment includes initial treatment with the composition containing the local anesthetic until the patient has become desensitized to the presence of capsaicin and subsequent treatment with a composition omitting the local anesthetic.

U.S. Pat. No. 5,134,166 discloses methods and compositions for treating certain allergy related condition and headaches using capsaicin in solution or suspension combined with a selected anesthetic, topical steroid or antihistamine.

U.S. Pat. No. 5,178,879 discloses clear, water-washable, non-greasy gels useful for topical pain relief containing capsaicin, water, alcohol and a carboxypoly-methylene emulsifier. A method of preparing the gels is also disclosed.

U.S. Pat. No. 5,560,910 discloses compositions and methods that are useful for topically treating inflammation caused by a wide variety of diseases. The compositions comprise an effective amount of a proteolytic enzyme, such as bromelain, in combination with capsaicin in a pharmaceutically acceptable carrier.

U.S. Pat. No. 5,910,512 discloses a water-based topical analgesic and method of application wherein the analgesic contains capsicum, capsicum oleoresin and/or capsaicin. This analgesic is applied to the skin to provide relief for rheumatoid arthritis, osteoarthritis, and the like.

U.S. Pat. No. 5,962,532 discloses a method of providing pain relief comprising administering an anesthetic along with injecting a composition of capsaicin.

U.S. Pat. No. 6,239,180 discloses a transdermal application of capsaicin in a concentration from greater than about 5 wt. % to about 10 wt. % for treating neuropathic pain. An anesthetic is initially administered to minimize the burning side effects from subsequent capsaicin application.

U.S. Pat. No. 6,348,501 discloses a lotion for treating the symptoms of arthritis using capsaicin and an analgesic along with a method for making such formulations.

U.S. Pat. No. 6,573,302 discloses a cream comprising: a topical carrier wherein the topical carrier comprises a member selected from the group comprising lavender oil, myristal myristate, and other preservatives in addition to hypericum perforatum arnica montana capric acid; and 0.01 to 1.0 wt. % capsaicin; 2 to 10 wt. % of an encapsulation agent selected from the group comprising colloidal oatmeal hydrogenated lecithin, dipotassium glycyrlhizinate and combinations thereof; esters of amino acid; a light scattering element having a particle size up to 100 nm.; and a histidine.

U.S. Pat. No. 6,593,370 discloses a topical capsaicin preparation for the treatment of painful cutaneous disorders and neural dysfunction. The preparation contains a nonionic, amphoteric or cationic surfactant in an amount effective to eliminate or substantially ameliorate burning pain caused by capsaicin.

U.S. Pat. No. 6,689,399 provides an anti-inflammatory composition for treatment of joint and muscle pain through transdermal delivery of a capsacinoid in conjunction with glucosamine. The ingredients of the composition of the present invention, namely, a capsacinoid in combination with a primary amine, such as glucosamine, at a high concentration.

US Patent Application 2005/0090557 relates to compositions of a TRPV1 agonist such as capsaicin, and a solvent system such as a penetration enhancer.

U.S. Patent Application 2006/0100272 discloses compositions and methods for the treatment of pain, and neuropathic pain in particular. The formulations are eutectic mixtures of a capsaicinoid and a local anesthetic agent and/or an anti-pruritic agent.

US Patent Application 2006/0148903 relates to a method of treating post surgical pain comprising administering at the surgical site, a dose of capsaicinoid gel.

U.S. Pat. No. 7,282,224 discloses a pain relief composition comprising an effective amount of a nerve inhibiting component, including capsaicin, a capsaicinoid or a capsaicin analogue, which numbs or inhibits the nerve endings that signal pain, in combination with at least one of the following: an effective amount of an inflammation control component which is designed to reduce immediate pain and discourage future pain in the joints and muscles; an effective amount of a cooling component; an effective amount of a heat minimizing or blocking component; an effective amount of a circulation increasing component which effectuates better penetration of the actives to the skin and nerves; and an effective amount of a soothing and anti-inflammatory complex for the joints and/or muscles comprising glucosamine sulfate or HCl, zingiber officiniale (ginger root) extract, methyl sulfonylmethane (MSM), *Polygonum cuspidatum*.

U.S. Pat. No. 7,632,519 discloses a variety of TRPV1 agonist compounds (capsaicinoids and their related esters) and formulations thereof.

U.S. Pat. No. 7,771,760 discloses topical oils of capsaicinoids comprising a capsaicinoid, a solvent capable of solubilizing the capsaicinoid, and a capsaicinoid crystallization inhibitor.

U.S. Pat. No. 7,943,166 relates to a method and liquid solvent system of penetration enhancers from 10% (w/v) to about 30% (w/v) of a TRPV1 agonist, such as capsaicin, where a single topical application of the liquid formulation results in pain relief for at least two weeks.

U.S. Pat. No. 7,943,666 discloses formulations of ester derivatives of capsaicin and ester derivatives of myristoleic acid. These derivatives are capable of reverting to the active parent compound following enzymatic or chemical hydrolysis. These derivatives have a higher lipophilicity, lipid solubility and less irritation to the skin than the parent compound, and hence are better able to be incorporated into certain pharmaceutical formulations, including cream and ointment pharmaceutical formulations. The disclosed pharmaceutical compositions are useful for pain management in mammals in vivo and have been contemplated to be used in the treatment of various pains in humans.

U.S. Pat. No. 8,703,741 relates to the use of vanilloid receptor agonist together with a glycosaminoglycan or proteoglycan for producing an agent for treating pain.

U.S. Pat. No. 8,802,736 relates to topical compositions of TRPV1 agonists.

Despite the advancements in the art, there remains a need for more effective pain-relieving capsaicinoid formulations.

OBJECTS OF THE INVENTION

It is an object of the invention to provide a topical pain relief composition that provides long-term pain relief without loss of sensation in the area treated.

It is an object of the invention to provide topical compositions of TRPV1 selective agonists such as capsaicin and other related compounds in preparations which eliminate or substantially ameliorates initial burning/stinging pain caused by the TRPV1 selective agonist compound observed following topical administration thereby making the preparation tolerable following initial and long-term use.

It is an object of the invention to provide topical TRPV1 selective agonist containing compositions such as capsaicin formulations for use in the treatment of joint pain, muscle pain, tendonitis, and for certain forms of localized neuropathic pains that are not amenable to treatment with currently marketed topical preparations, and do not have the side effects of systemic treatments.

It would be advantageous to provide methods and compositions containing compositions such as capsaicin or analogues thereof, at therapeutically effective concentrations to cause a pain relieving effect without the side effects normally associated with the use of capsaicinoids.

It is therefore an object of the present invention to provide methods for administering capsaicin or capsaicin analogues topically at high concentrations to achieve a prolonged pain reduction effect but without the severe burning sensation that occurs following topical application.

It is yet another object of the present invention to provide compositions containing agents to complement the remedial properties of capsaicin, or related compounds, for the treatment of pain of the joints and muscles and other medical conditions, where the agents are conveniently administered with the capsaicin.

It is yet another object of the present invention to provide a composition and method for topically treating pain and inflammation that is safe and effective and does not have the side effects of opioids or conventional NSAIDS.

It is another object of this invention to provide solvent systems that solubilize appreciable concentrations of the relatively aqueous insoluble TRPV1 selective agonists (such as capsaicin) to produce compositions such that solvent systems contains analgesic and anti-inflammatory ingredients that rapidly penetrate the layers of skin to mitigate the stinging and burning pain resulting from the topical application of the significant capsaicin concentrations, and that can improve storage stability.

Other objects and advantages of the present invention will be apparent from a review of the following specification.

SUMMARY OF THE INVENTION

The invention relates to a composition comprising:
i) 0.075-20% by weight of a capsaicinoid,
ii) an extended release agent to slow the release of said capsaicinoid from said composition upon administration of said composition to a mammal, and
iii) a surfactant,
wherein said composition reduces or eliminates the burning and stinging created by said capsaicinoid upon topical administration.

In another embodiment, the invention is a composition comprising:
i) 0.075-20% by weight of a capsaicinoid,
ii) 70-99.925% by weight of an aqueous vehicle comprising a nonionic surfactant (for dissolving the capsaicinoid or for forming an emulsion) or for maintaining a stable solution, and an extended release agent to slow the release of said capsaicinoid from said aqueous composition upon topical administration of said composition in a mammal, wherein said aqueous vehicle reduces or eliminates the burning and stinging created by said capsaicinoid upon topical administration.

In an advantageous embodiment, the capsaicinoid is 2-30% by weight capsaicinoid, and the extended release agent is hyaluronic acid, at 0.5-1.5° % by weight of the composition. Advantageously, the hyaluronic acid is a mixture of both low molecular weight hyaluronic acid and high molecular weight hyaluronic acid. In another embodiment, the extended release agent is collagen or elastin.

In other advantageous embodiments, the invention includes a solvent/penetration enhancer such as DGME, ethanol and/or propylene glycol, an analgesic or anesthetic agent such as methyl salicylate, camphor, menthol, icilin, eucalyptol and/or phenol; or an anti-inflammatory agent, such as a flavonoid, a steroid, and/or an NSAID.

Advantageous embodiments of the compositions of the invention include.

a composition comprising:
  i) a capsaicinoid,
  ii) an extended release agent,
  iii) a surfactant, and
  iv) a penetration enhancer;
a composition comprising:
  i) 0.2-20% by weight of capsaicinoid,
  ii) 0.1-0.5% by weight of said extended release agent,
  iii) 0.5-15% by weight nonionic surfactant;
a composition comprising:
  i) 2-20% by weight of capsaicinoid,
  ii) 0.2-0.5% by weight of hyaluronic acid, and
  iii) 2-15% by weight nonionic surfactant; and
a composition comprising:
  i) 0.20-20% by weight of a capsaicinoid,
  ii) 0.1-0.5% by weight hyaluronic acid,
  iii) 2-15% by weight PS 80 or polyoxy 40 hydrogenated castor oil, and
  iv) 1-40% by weight penetration enhancer.

The invention also includes:
a method of formulating an aqueous capsaicinoid formulation comprising:
  i) dissolving a capsaicinoid in a surfactant to form a solution, and
  ii) adding an aqueous solution of hyaluronic acid to the solution of step i);
a method of producing an aqueous topical formulation of capsaicin comprising:
  i) mixing a capsaicinoid, a surfactant and a penetration enhancer, and
  ii) adding an aqueous solution of hyaluronic acid to the product of step i); and
a method of producing an aqueous topical formulation of capsaicin comprising:
  i) mixing a capsaicinoid, and a penetration enhancer, and
  ii) adding an aqueous solution of hyaluronic acid to the product of step i),
  iii) adding a surfactant to the product of step ii).

The invention also relates to methods of making and using compositions for the treatment of pain such as joint pain (e.g. arthritis pain), muscle pain, as well as treating a variety of other medical conditions. A method of treating itching or fingernail or toenail fungus in a mammal is also included. Typically, administration is topical application to the affected area.

Methods of treating pain in a mammal (e.g. human) comprise topically administering the compositions of the invention, and include methods of reducing the density of nociceptor nerve fibers in the dermis and epidermis of a selected region of a mammal, comprising administering the composition of the invention to said region, e.g. where the density of functional nociceptive nerve fibers is decreased by at least 20%, 30%, 40% or 50% after topically administering the composition.

The invention includes methods of treating a capsaicin responsive condition such as pain including neuropathic pain, inflammatory hyperalgia, vulvodynia, interstitial cystitis, rhinitis, burning mouth syndrome, oral mucositis, herpes, dermatitis, pruritis, tinnitus, psoriasis, or headaches, with the compositions of the invention.

Lastly, the invention also relates to kits comprising the liquid formulation of the invention and a non-occlusive applicator device. In another embodiment the kit further comprises a cleaning solution for removal of residual agonist.

DETAILED DESCRIPTION OF THE INVENTION

The invention provides topical pharmaceutical compositions containing a therapeutically effective amount of a TRPV1 agonist, an extended release agent such as hyaluronic acid, a surfactant, and optionally, one or more penetration enhancers. The pharmaceutical composition is in a form suitable for topical administration to a mammal, typically human. The concentration of capsaicin is typically greater than 0.02 wt. % and less than 20 wt. % of the formulation.

In one embodiment, the composition comprises a capsaicinoid, hyaluronic acid, a surfactant and one or more penetration enhancers, where said surfactant and one or more penetration enhancers, taken together, constitute at least about 20% by wt., at least about 50% by wt., and up to 70% by wt. of the formulation.

Penetration enhancers can be an ether, or an alcohol. The formulation can contain one or more penetration enhancers selected from the group consisting of propylene glycol, ethyl alcohol, diethylene glycol monomethyl ether (DGME), and dimethyl sulfoxide, and can contain a nonionic surfactant e.g.s. PS-80 and polyoxy-40 Hydrogenated Castor Oil.

In an advantageous embodiment, a 0.4 wt. % hyaluronic acid water solution composed of a mixture containing 70 wt. % hyaluronic acid with a molecular weight ~11 kDaltons and 30 wt. % hyaluronic acid with a molecular weight of ~1,000 kDaltons was added to an alcohol mixture solution containing 0.25 wt. % to 10 wt. % capsaicin dissolved in solublizing and penetrating agents consisting of ethyl alcohol, propylene glycol and PS80 and/or polyoxy 40 hydrogenated castor oil (balance water). The mixture resulted in an optically crystal clear and moderately viscous solution. Adjusting the relative percentages of the hyaluronic acid molecular weights and surfactant composition resulted in variation of viscosity of the mixture.

Capsaicin formulations of 0.25% wt. % to 10 wt. % as described in the foregoing paragraphs was applied to knees, arms of several subjects via a 3.7 ml roller-ball vial (See Examples). The applied liquid film dried rapidly and minimal discomfort from burning and stinging was experienced. The formulations were relatively odor free.

Surprisingly, using the methods and compositions of the invention in humans results in less pain or discomfort than administration of conventional capsaicin formulations containing much lower concentrations of capsaicin. Example 2 below shows that, 0.25 wt. % capsaicin liquid formulation produced less burning and stinging than a common liquid capsaicin formulation containing 0.15 wt. % capsaicin.

The invention provides methods for administration of a TRPV1 agonist such as capsaicin, at a concentration of greater than 1% by wt., greater than 2%, greater than 5%, greater than 8%, or even greater than 10% by wt., without significant burning and stinging.

Compositions of the Invention

The invention relates to compositions, advantageously liquid aqueous solutions, comprising a TRPV1 selective agonist, and a surfactant capable of solubilizing said TRPV1 selective agonist, wherein said composition has an amount of TRPV1 selective agonist sufficient to decrease the density of functional nociceptive nerve fibers when said composition is applied topically, and said composition has an amount of a extended release agent and surfactant sufficient to eliminate or reduce the burning and/or stinging sensation or erythema created by the topical administration of the TRPV1 selective agonist. The liquid solution of the invention is advantageously an aqueous solution.

The TRPV1 selective agonists, hyaluronic acid or other extended release agents, surfactants, and excipients suitable for use in the pharmaceutical compositions of the present invention, are those which are pharmaceutically acceptable when applied to human skin, i.e. having acceptable toxicity at the levels used. All components of the formulations of the invention are USP grade. In a preferred embodiment of the invention, the compositions are manufactured in full compliance with GMP regulations of the U.S. FDA.

In one embodiment, the amount of TRPV1 selective agonist sufficient to decrease the density of functional nociceptive nerve fibers by at least 20%, or at least 50%, after topical application. In another embodiment the composition is 0.20-30% by weight of the TRPV1 selective agonist. The TRPV1 selective agonist can be a vanilloid, or in an advantageous embodiment, a capsaicinoid such as capsaicin.

When combined with ingredients disclosed herein, the amount of TRPV1 selective agonist, e.g. a capsaicinoid (e.g. trans-capsaicin) in the topical preparation can be from 0.075-30 wt. %, 0.2 wt. % to 30 wt. %, between 1 wt. % and 20 wt. %, e.g. 1 wt. %, 5 wt. %, 10 wt. %, and 20 wt. %.

The capsaicinoid is prepared for topical application by being incorporated into a pharmaceutically and physiologically acceptable aqueous vehicle for administration with diminished burning sensation upon application. The present invention is directed to the topical administration of capsaicin into discrete localized areas for the treatment and lessening of pain. Significant advantages result from the application of milligram quantities of capsaicin in order to produce therapeutic results through alteration of sensory nerve function (TRPV-1) in a limited area.

The invention relates to compositions, typically liquid solution pharmaceutical formulations, of a TRPV1 selective agonist (i.e. acting as specific agonist for TRPV1 as capsaicin does) such as capsaicinoid or a capsaicin analogue, primarily for the treatment of pain. The compositions include one or more extended release agents and a surfactant which reduce or eliminate the burning or stinging pain caused by administration of the TRPV1 selective agonist, thereby making the TRPV selective agonist formulation administration tolerable, including in long-term administration. The present application discloses the discovery that a TRPV1 selective agonist containing topical composition is very effective in treating pain in humans and causes significantly less burning pain at the site of the application, when administered with a extended release agent and a surfactant, than the same composition without such components.

The present invention provides the long lasting pain relief afforded by the TRPV1 selective agonist, e.g. capsaicin, without the same severity of concentration-dependent capsaicin side effects (e.g. stinging and burning) associated with prior art capsaicin formulations. The formulations can provide pain relief for periods of weeks to months dependent upon disease state and severity. Importantly, unlike anesthetics and opioids, the formulations of the present invention do not diminish or eliminate tactile sensation in the skin onto which the formulation has been topically applied.

The topical formulations, particularly for the treatment of pain, contain higher levels of TRPV1 selective agonists such as capsaicin, than normally used. The subject formulations do not have the discomfort and burning associated with capsaicin formulations of the prior art. The formulations of the TRPV1 selective agonist can include anti-inflammatory, and other additives that contribute to pain relief and the therapeutic treatment of pathological conditions such as arthritis pain, osteoarthritis, joint disorders, muscular pain, neuropathic pain, neck and back pain, shingles, cluster headaches and other disease or health-related conditions.

The subject invention relates to pharmaceutical topical compositions for delivery of significant quantities of a TRPV1 selective agonist compound such as capsaicin or related compounds via the skin. The components of the composition other than the TRPV1 selective agonist compound are included to reduce or eliminate the burning sensation associated with administration of the TRPV1 selective agonist compound as well as to enhance skin penetration of said TRPV1 selective agonist compound. The additional components are typically hyaluronic acid and a nonionic surfactant such as PS 80, which are generally accepted as safe.

It has been discovered that incorporation of a sufficient quantity of these ingredients into the capsaicin preparations forms a mixture for the topical treatment of pain such that the initial burning/stinging pain resulting from capsaicin is eliminated or ameliorated. Water concentrations are typically 30-60 wt % or 40-60 wt % of the preparations and can exceed 50% or even 55 wt % of the formulations.

It has been demonstrated that these ingredients reduce the burning/stinging sensation produced following topical application of a TRPV1 selective agonist compounds such as capsaicin. The compositions of the invention include appreciable quantities of hyaluronic acid and a surfactant, and optionally phenol which minimizes the burning/stinging sensation produced following topical application capsaicin. Components can also be added which enhance the penetration of the capsaicin into the viable layers of the skin and into subcutaneous tissues.

Accordingly, the present invention provides topical preparations comprising an amount of a TRPV1 selective agonist such as capsaicin effective in initial and long-term or repeated administration to reduce pain associated with certain cutaneous disorders and neural dysfunctions.

The components of the formulations of the invention are discussed below.

TRPV1 Selective Compounds including Capsaicinoids

For a general discussion of TRPV1 agonists including capsaicinoids of the invention, see US patent application 2008/0262091, and commonly owned U.S. Ser. No. 13/609,100, each of which is hereby incorporated by reference in its entirety. The term "capsaicinoid" as used herein includes capsaicin, a capsaicinoid other that capsaicin, i.e. dihydrocapsaicin, nordihydrocapsaicin, homodihydrocapsaicin, homocapsaicin, and nonivamide, and a mixture of capsaicin with one or more other capsaicinoids. The amount of drug used being based on a therapeutically dose to a dose of capsaicin. Capsaicin is practically insoluble in water, but freely soluble in ethyl alcohol, diethylene glycol monoethyl ether (DGME), dimethyl sulfoxide (DMSO) and propylene glycol. Capsaicin is a lipophilic white crystalline powder; melting point 60-65 degrees C.

Alternatively, a "capsaicin analogue" such as resiniferatoxin, can be administered in place of part or all of the capsaicinoid. The amount of analogue administered being the therapeutically equivalent dose of capsaicin-see US patent application 2008/0262091, hereby incorporated by reference in its entirety. In another embodiment, a TRPV1 agonist other than a capsaicinoid, or capsaicin analogue, is utilized in the formulations and methods of the invention.

According to the present invention, the pain relief composition comprises a therapeutically effective amount of a nerve-inhibiting component—a TRPV1 selective agonist, which inhibits the nerve endings that signal pain. The TRPV1 selective agonist component is typically a vanilloid, a capsaicinoid, more specifically capsaicin, nonivamide or other capsaicin analogue, or a mixture thereof.

TRPV1 selective agonist compounds of the subject invention include the natural capsaicinoids (Capsaicin Oleoresin), and synthetic (Nonivamide) forms, as well as analogues of capsaicin. Capsaicin is known by the chemical name N-(4-hydroxy-3-methoxybenzyl)-8-methylnon-trans-6-enamide. Capsaicin is the main capsaicinoid (typically 69%) in chili peppers, followed by dihydrocapsaicin (typically 22%) and norihydrocapsaicin (typically 7%). Nonivamide is found in trace amounts in chili peppers.

Capsaicin and dihydrocapsaicin together make up 80-90% of the capsaicinoids found in chili peppers. The different capsaicinoid compounds have slight structural variations in the hydrocarbon tail, changing their ability to bind to the nerve receptors and their ability to penetrate layers of receptors on the tongue, mouth, and throat.

Capsaicinoids are very similar in structure, varying only by the length of along hydrocarbon portion (that is, a portion containing only carbon and hydrogen atoms), and by the presence or absence of one carbon-to-carbon double bond in that hydrocarbon portion (carbon-carbon double bonds).

TABLE 2

CAPSAICIN & CAPSAICINOID PROPERTIES

| Capsaicinoid Name | Abbr. | MW | Natural Relative Amount | Scoville Heat Units | Molecular Formula | Chemical Structure |
|---|---|---|---|---|---|---|
| Capsaicin | C | 305 | 69% | $16 \times 10^6$ | $C_{18}H_{27}NO_3$ | 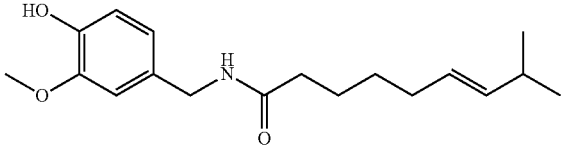 [SMILES: COc1cc(CNC(=O)CCCC/C=C/C(C)C)ccc1O] |
| Dihydrocapsaicin | DHC | 307 | 22% | $15 \times 10^6$ | $C_{18}H_{29}NO_3$ | 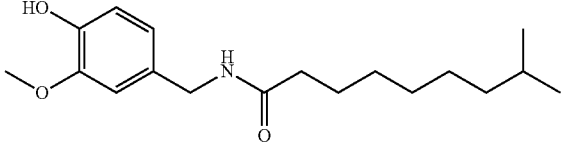 [SMILES: COc1cc(CNC(=O)CCCCCCC(C)C)ccc1O] |
| Nordihydrocapsaicin | NDHC | 293 | 7% | $9.1 \times 10^6$ | $C_{17}H_{27}NO_3$ | 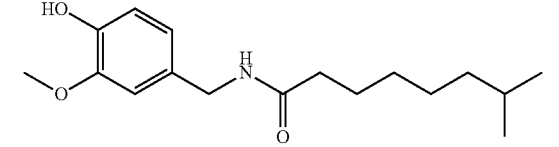 [SMILES: COc1cc(CNC(=O)CCCCCC(C)C)ccc1O] |
| Homodihydrocapsaicin | HDHC | 321 | 1% | $8.6 \times 10^6$ | $C_{19}H_{31}NO_3$ | 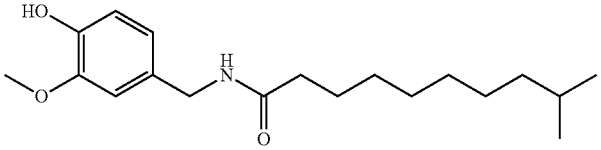 [SMILES: COc1cc(CNC(=O)CCCCCCCC(C)C)ccc1O] |
| Homocapsaicin | HC | 319 | 1% | $8.6 \times 10^6$ | $C_{19}H_{29}NO_3$ | 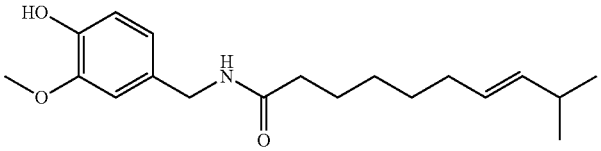 [SMILES: COc1cc(CNC(=O)CCCCC/C=C/C(C)C)ccc1O] |
| Nonivamide | PAVA | 293 | [1]0.25% | $9.2 \times 10^6$ | $C_{17}H_{27}NO_3$ | 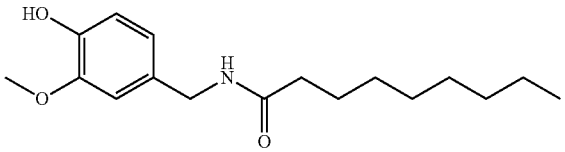 [SMILES: CCCCCCCCC(=O)NCc1ccc(O)c(OC)c1] |

[1]Constant et al. J. Nat. Prod. 1996, 59, 425-426

As noted above in TABLE 2, capsaicin and several related compounds are called capsaicinoids. Nonivamide, the vanillylamide of n-nonanoic acid (also PAVA) is used as a reference substance for determining the relative pungency of capsaicinoids as well as being used as a food additive to add pungency.

Both the naturally occurring capsaicin and the synthetic versions that differ slightly in their alkyl chain, have similar pharmacological effects.

Nonivamide is present in chili peppers but is commonly manufactured synthetically. It is more heat-stable than capsaicin. Ointments sold to relieve arthritis and muscle pain often contain nonivamide. Application of the ointment on the skin is claimed to result in a warm to burning sensation and pain relief for several hours.

Resiniferatoxin (RTX) is a very potent capsaicin analogue. Other TRPV1 selective agonists include anandamide, and NADA. Many additional agonists are disclosed in U.S. Pat. Nos. 7,943,166 and 7,632,519, each of which is hereby incorporated by reference in its entirety. Some capsaicin analogues are described in U.S. Pat. No. 5,962,532, hereby incorporated by reference in its entirety.

The formulations of the invention typically include 0.075-30% by weight, 0.2-30%, or 2-20%, 2-10% or 5-15% of a capsaicinoid (e.g. capsaicin), or related compounds. When the TRPV1 selective agonist is other than capsaicin, since potency can vary, the amount of agonist in the formulation is that amount which achieves the same results achieved by the weight percent ranges noted herein for capsaicin.

Extended Release Agents

It has been found that inclusion of certain compounds which slow the release of a capsaicinoid from the formulation (causing extended release), result in diminished burning and stinging effects. Advantageously, the extended release agent will release said capsaicinoid over a period of greater than 15 minutes, 30 minutes, 1 hour, or greater than 4 hours. In one embodiment, the capsaicinoid is released over a period greater than a week. Typically a higher dose will be released over a longer time period. In one embodiment of the invention, the extended release agent is not a glycosaminoglycan or a proteoglycan.

Hyaluronic Acid

The molecular weight of hyaluronic acid (HA) of the invention advantageously ranges from 3 kDaltons to 1,000 kDaltons. In certain embodiments, the formulations can include "high" molecular weight hyaluronic acid of greater than 800 kDaltons, i.e. 1000, 2000, 3000, 4000 or 5000 kDaltons. In certain embodiments, the formulations can include "low" molecular weight hyaluronic acid of less than 200 kDalton, advantageously less than 20 kDalton, more advantageously less than 15 kDalton. The hyaluronic acid component of the solubilized capsaicin formulations forms a polysaccharide network within the aqueous solution that contributes to a delayed and prolonged release of capsaicin thus contributing to minimizing the discomfort from the application of capsaicinoid.

HA has been extensively utilized in cosmetic products because of its viscoelastic properties and excellent biocompatibility. Application of HA containing cosmetic products to the skin is reported to moisturize and restore elasticity thereby achieving an anti-wrinkle effect.

The high solubilization of capsaicin using the nonionic surfactants PS 80 and/or Cremophor RH 40, together with hyaluronic acid, a substance that is naturally present in the human body that occurs in various tissues (skin, synovial fluids of joints and connective tissues), contribute to ameliorating the burning and stinging associated with capsaicin formulations. In an advantageous embodiment, <0.5 wt. % hyaluronic acid and its salts (0.35 wt. % HA<50 kDaltons and ~0.15 wt. % HA ranging from 800 to 1,200 kDaltons), significantly contributes to a reduction in the capsaicin associated burning and stinging reaction. The high MW hyaluronic acid used in the Examples herein had an average molecular weight of 1000 kDaltons. While not wishing to be bound by theory, it is believed that the addition of the hyaluronic acid component to the capsaicin forms a polysaccharide network within the aqueous solution that causes capsaicin to be released more slowly in a controlled manner that results in a lessening of the burning and stinging pain.

The physiological function of the stratum corneum, the outermost and non-viable layer of the skin, is to act as a protective barrier for the body and as such it is particularly effective at preventing the permeation of hydrophilic molecules including some drugs into deeper skin layers, where viable cells are located. Low molecular weight (MW) HA provides better penetration abilities than higher MW HA and, accordingly, influenced the expression of many genes including those contributing to keratinocyte differentiation and formation of intercellular tight junction complexes which are reported to be reduced in aged and photo-damaged skin. These different molecular properties of high and low MW HA generated different in-vivo effects with pronounced moisturization and elasticity properties shown for high MW HA and marked reduction of wrinkles demonstrated for low MW HAs. The increased activity at decreasing molecular weight can be explained by the more efficient skin penetration of the smaller HA molecules. (Farwick, M., et al. *Low Molecular Weight Hyaluronic Acid: Its Effects on Epidermal Gene. Expression and Skin Aging*, International Journal for Applied Science.)

Low molecular weight hyaluronic acid can penetrate the epidermal layer of the skin and seep into a deeper region, where it supplements the water loss and helps restore the natural cell regenerative qualities in skin. The high MW hyaluronic acid works on the epidermal level and offers a protective effect, hydrating and healing the protective barrier of the skin. This provides a smoother skin surface. Combining the low and high HA molecular weights utilizes the unique characteristics and benefits of the two types of HA to reduce the burning and stinging effects of capsaicinoids.

Advantages of HA for dermal administration of capsaicin are: surface hydration and film formation enhance the permeability of the skin to topical drugs, it promotes drug retention and localization in the epidermis; and it exerts an anti-inflammatory action (medium and high-molecular-weight HA). In one embodiment of the invention, the hyaluronic acid is in the form of a cross-linked hydrogel.

Collagen and Elastin

Collagen is the main structural protein of the various connective tissues in animals. As the main component of connective tissue, it is the most abundant protein in mammals, making up from 25% to 35% of the whole-body protein content. Collagen, in the form of elongated fibrils, is mostly found in fibrous tissues such as tendons, ligaments and skin, and is also abundant in corneas, cartilage, bones, blood vessels, the gut, and intervertebral discs.

Elastin is a protein in connective tissue that is elastic and allows many tissues in the body to resume their shape after stretching or contracting. Elastin helps skin to return to its original position when it is poked or pinched. Elastin is also an important load-bearing tissue in the bodies of vertebrates and used in places where mechanical energy is required to be stored.

Collagen and/or elastin with a capsaicinoid is advantageous in the treatment of pain including OA pain. The addition of the collagen and/or elastin component to a solubilized capsaicin formulation forms a protein network within the aqueous solution that contributes to a delayed and prolonged release of capsaicin thus contributing to minimizing the burning discomfort from either topical application or injection of capsaicin. Additionally, upon injection with a capsaicinoid these naturally occurring high molecular weight proteins function to control the rate of capsaicin release to the nerves to reduce burning, provide lubrication to the sliding bone surfaces as well as provide building materials for bone cartilage repair. Addition of hyaluronic acid to capsaicinoid formulations containing either or both these naturally occurring high molecular weight proteins further optimizes tolerability and efficacy. In the compositions of the invention, the collagen or elastin must be in the form of a liquid or gel.

Bioresorbable Polymer Matrix

A bioresorbable polymer matrix, e.g. a cross-linked oxidized dextran hydrogel, can also be used in the formulations of the invention as the extended release agent. See U.S. Pat. No. 8,435,565 hereby incorporated by reference in its entirety.

Surfactants

One or more surfactants, advantageously non ionic (e.g. polysorbates such as PS80, Cremophor® RH 40 (polyoxy 40 hydrogenated castor oil), sorbitan esters (Spans), poloxamers, cetyl alcohol, cetostearyl alcohol, polyethoxylated alcohols, polyoxyethylene sorbitan, octoxynol, stearyl alcohol etc.), can be also be added to the compositions of the invention to solubilize the capsaicinoid and enhance the skin penetration of the capsaicinoids. They can ameliorate the initial stinging pain caused by capsaicin (or related compounds) in admixture with the pharmaceutically acceptable carrier ingredients for topical administration. Fatty acid ester non-ionic surfactants that are utilized in pharmaceutical, cosmetics and foodstuffs are advantageous because of the compatibility with biological tissues.

A surfactant, such as a nonionic surfactant, e.g. PS 80 and/or Cremophor® RH 40 (polyoxy 40 hydrogenated castor oil) (alternatively, Solute® HS 15), can be combined with hyaluronic acid and one or more of the pharmaceutically acceptable vehicles described herein so that the surfactant serves as a wetting agent, solubilizer, and emulsifier and contribute to minimizing the stinging or burning discomfort associated with capsaicinoid administration.

Further, surfactant/capsaicin (or other capsaicinoid(s)) concentrates can be formed for use in the formulations and methods of the invention as described in commonly owned U.S. Pat. No. 8,637,569 hereby incorporated by reference in its entirety.

In one embodiment of the invention, a surfactant is not present in the composition. An example is where the capsaicinoid concentration is less than 0.25% by wt.

Examples of formulations of the invention with the surfactant PS 80 are shown below:

| 2%, 5%, and 10% CAPSAICIN-HA FORMULATIONS (Optically Clear Single Phase Formulations) | | | |
|---|---|---|---|
| INGREDIENTS | 2 wt. % HA-Cap | 5 wt. % HA-Cap | 10 wt. % HA-Cap |
| CAPSAICIN (Formosa) | 2 | 5 | 10 |
| POLYSORBATE 80 (Super Refined - Croda) | 7 | 10 | 13 |
| ETHYL ALCOHOL (Grain Alcohol) | 20 | 20 | 20 |
| ETHOXYDIGLYCOL METHYL ETHER (DGME) | 10 | 10 | 10 |
| PROPYLENE GLYCOL | 10 | 10 | 10 |
| (1)HA (~1,000K Daltons) | 0.17 | 0.17 | 0.12 |
| (1)HA SLMW (~20K Daltons) | 0.33 | 0.33 | 0.25 |
| (1)DISTILLED WATER | 50.50 | 44.50 | 36.63 |
| TOTAL | 100 | 100 | 100 |

Examples of formulations of the invention with the surfactant Cremophor RH 40 are shown below:

| HA-CAPSAICIN FORMULATIONS | | | | | | |
|---|---|---|---|---|---|---|
| INGREDIENTS | ¼% Cap-HA (wt. %) | 2% Cap-HA (wt. %) | 5% Cap-HA (wt. %) | 10% Cap-HA (wt. %) | 15% Cap-HA (wt. %) | 20% Cap-HA (wt. %) |
| CAPSAICIN (Formosa) | 0.25 | 2 | 5 | 10 | 15 | 20 |
| CREMOPHOR RH 40 | 5 | 7 | 10 | 12 | 16 | 16 |
| ETHYL ALCOHOL (Grain Alcohol) | 20 | 20 | 20 | 20 | 20 | 20 |
| ETHOXYDIGLYCOL (DGME) | 10 | 10 | 10 | 10 | 10 | 10 |
| PROPYLENE GLYCOL | 10 | 10 | 10 | 10 | 10 | 10 |
| (1) HYALURONIC ACID AQUEOUS SOLUTION | 54.75 | 51 | 45 | 38 | 29 | 24 |
| TOTAL | 100 | 100 | 100 | 100 | 100 | 100 |

Note:
(1) The Hyaluronic Acid Aqueous Solution contains 0.65 wt.% Hyaluronic Acid SLMW (~20K Daltons), 0.35 wt. % Hyaluronic Acid 1,000K Daltons) and 99 wt. % Distilled Water.

Agents that Enhance Skin Penetration

Diethylene glycol monoethyl ether (DGME) is a penetration enhancer (and solvent) useful in the formulations of the invention. It is commercially available as Transcutol® (Gattefossé Corp., Paramus, N.J.). DGME is both an effective solvent and penetrating agent for capsaicinoids. Other penetrating agents include propylene glycol, ethoxydiglycol, and dimethyl isosorbide, each known in the art of topical formulation development to enhance skin penetration.

Alcohols including ethyl alcohol, benzyl alcohol, glycerol, propanol, isopropyl alcohol, polyethylene glycol, polyethylene glycols, etc. can be added to the formulations as effective capsaicin solubilizing and penetrating agents. Addition of an alcohol results in compositions with lower viscosity and shorter drying times.

Dimethyl sulfoxide (DMSO) is an organosulfur compound with the formula $(CH_3)_2SO$. This colorless liquid is an important polar aprotic solvent that dissolves both polar and nonpolar compounds and is miscible in a wide range of organic solvents as well as water. It penetrates the skin very readily and has the unusual property that many individuals perceive a garlic-like taste in the mouth after contact of DMSO with the skin.

Analgesic Agents

The compositions of the subject invention also include an analgesic agent—one or more analgesics. As used herein, an "analgesic agent" is a compound or compounds which, when topically applied, reduces pain or burning sensation without loss of tactile sensation. The analgesics agents of the invention do not include a capsaicinoid and do not include an opioid. Further, the analgesic agents do not include a topical local anesthetic, such as lidocaine (or procaine, amethocaine, cocaine lidocaine (also known as Lignocaine), prilocaine, bupivacaine, levobupivacaine, ropivacaine, mepivacaine, dibucaine) in the TRPV1 specific agonist containing formulations. These caine local anesthetics have not been effective in sufficiently moderating the burning effect of capsaicin when administered concomitantly with capsaicin topically; they have a slower onset of action relative to capsaicin. To reduce the burning sensation, these caine local anesthetics are typically administered in advance of capsaicin attempting to elicit sufficient anesthetic action prior to the burning sensation associated with capsaicin.

The present application includes the discovery that topical TRPV1 selective agonist containing compositions have significantly less burning pain at the site of the application when combined with topical analgesic and/or anesthetic agents (when compared to the same composition without analgesic and/or anesthetic agents), and are extremely effective in treating pain in mammals including humans. As used herein, "topical" refers to administration of the composition to a defined area of the body such as a defined area of skin surface or mucous membrane.

Menthol

Menthol is an organic compound made synthetically or obtained from peppermint or other mint oils that produces a feeling of cooling. Advantageously, (1)-menthol (natural menthol derived from peppermint oil) is used in the subject invention for analgesic effects. Alternatively, another transient receptor potential subfamily M8 (TRPM8) agonist such as icilin or eucalyptol can be used.

The formulations of the invention can include 1-20%, 5-15% by wt, or 10-20% by weight menthol.

Methyl Salicylate and Camphor

The formulations can also include methyl salicylate (1-20% by wt, 5-15% by wt, or 10-20% by wt), and camphor (1-20% by wt, 2-10% by wt, or 10-20% by wt). See Examples 12 and 13 below.

Phenol

Phenol cools and numbs skin on contact, making it an effective topical analgesic ingredient. It also kills germs, and reduces the risk for infection in minor skin irritations. It has been used medically for over 100 years, for these and other applications. Because it can improve the effectiveness of a preparation at relieving itching, phenol is added to formulations meant for the relief of insect bites and stings, sunburn, and other painful and itchy skin conditions.

The formulations of the invention can include 0-4.6 wt. %, advantageously 0.1-0.5 wt. % phenol.

Eugenol/clove oil and thymol/thyme oil can be added in addition to, or as alternative to phenol.

Anti-Inflammatory Agents

An effective amount of an inflammation control component, which reduces or relieves inflammation, swelling, redness, and/or pain in the joints and muscles associated with inflammation, can be added.

Anti-Inflammatory Polyphenols and Sesquiterpenes

Many polyphenols are known to have anti-inflammatory activity. Examples are flavonoids (e.g. apigenin) and curcumin. Apigenin offers some of nature's most potent and effective anti-inflammatory and anti-oxidant properties. It can be included in the formulation to further enhance therapeutic efficacy. Apigenin has a broad range of anti-inflammatory properties and has been cited for the ability to block the production of compounds that cause pain; e.g., the arthritis causing substance cyclooxygenase (COX). The addition of apigenin to a mixture of capsaicin in the constituents of the subject pain relieving formulations can be accomplished using the high temperature surfactant technology where apigenin is first dissolved in PS80 at elevated temperatures to form a concentrate that is then added to the mixture (see US Application US 2011/0311592 A1).

αBisabolol is another potent anti-inflammatory sesquiterpene which is known to also have anesthetic, anti-irritant, anti-inflammatory, anti-fungal and anti-microbial properties. αBisabolol is also demonstrated to enhance the percutaneous absorption of certain molecules. αBisabolol helps transport active ingredients transdermally by enhancing skin penetration. (R. Kadir and B. W. Barry. *Alpha-Bisabolol, a Possible Safe Penetration Enhancer for Dermal and Transdermal Therapeutics. Int. J Pharm.* 70:87-94 (1991).)

NSAIDs/Diclofenac Sodium

In further embodiments of the invention, a Non-Steroidal Anti-Inflammatory Agent (NSAID) is co-administered with the TRPV-1 selective agonist formulations. The NSAID and the TRPV-1 selective agonist can be administered together as a single composition (where a topical NSAID is used) or administered as separate compositions (where a topical or not topical NSAID is used). The NSAID can be administered before, after or at the same time as the TRPV-1 selective agonist by the same or different routes of administration. For example, the TRPV-1 selective agonist can be administered topically while the NSAID agent can be administered orally, topically or parentally. NSAIDs useful as adjunctive agents in the formulations of the present invention include aspirin (acetylsalicylic acid), ibuprofen, naproxen, diclofenac, benoxaprofen, ketoprofen, indomethacin etc., and mixtures thereof. As used herein, "NSAID" does not include methyl salicylate.

Combining an NSAID such as a diclofenac salt with capsaicin in a topical formulation combines two established pain relieving agents which function via two different mechanisms of action (MOAs); i.e., TRPV1 nerve defunctionalizer and a potent COX-2 inhibitor. Solubility studies were conducted (see below) and formulations were prepared containing the NSAID, diclofenac sodium, together with the TRPV1 selective agonist, capsaicin, utilizing the subject invention.

TABLE 3 lists components of several prepared capsaicin formulations. These formulations are discussed in the Examples.

TABLE 3

Ingredients Of Capsaicin Topical Formulations

| Topical Ingredients | Ingredient Ranges (Wt. %) | Function | No. 1 0.25% Cap Form 2 (Wt. %) | No. 2 0.25% Cap-HA Form 2 (Wt. %) | No. 3 2% Cap-HA Form 2 (Wt. %) | No. 4 2% Cap-HA Form 3 (Wt. %) | No. 5 5% Cap-RA Form 2 (Wt. %) | No. 5A 5% Cap-HA Form 2 (Wt. %) | No. 6 10% Cap-HA Form 2 (Wt. %) |
|---|---|---|---|---|---|---|---|---|---|
| (1) Capsaicin | 0.1-10 | Defunctionalization of TRPV-1 sensory neurons | 0.25 | 0.25 | 2.0 | 2.0 | 5.0 | 5.0 | 10 |
| Hyaluronic Acid ~1,000K Daltons | 0-0.5 | Viscosity enhancer & moisturizing agent | — | 0.20 | 0.15 | 0.10 | 0.15 | 0.15 | 0.15 |
| Hyaluronic Acid ~11K Daltons | 0-0.5 | Viscosity enhancer & moisturizing agent | — | 0.30 | 0.35 | 0.40 | 0.35 | 0.35 | 0.35 |
| Ethyl Alcohol | 1-20 | Solvent | 20 | 20 | 20 | 20 | 20 | 20 | 20 |
| DGME | 0-10 | Solvent & penetration enhancer | 10 | 10 | 10 | 10 | 10 | 10 | 10 |
| Propylene Glycol | 0-10 | Solvent & penetration enhancer | 10 | 10 | 10 | 10 | 10 | 10 | 10 |
| (2) Polysorbate 80 | 0-15 | Surfactant, emulsifier & solubilizing agent | — | — | 2 | 2 | — | 10 | — |
| (3) PEG-40 Hydrogenated Castor Oil | 0-15 | Surfactant, emulsifier & solubilizing agent | — | 0.50 | 5 | 5 | 10 | — | 15 |
| Water | 30-60 | Solvent | q.s. | q.s. | q.s. | q.s. | q.s. | q.s. | q.s. |

Note:
(1) Trans-Capsaicin, Aversion Technologies Inc., 95.7% Trans-Capsaicin, Balance Cis-Capsaicin, USP 30
(2) Super-refined Polysorbate-80, Croda Inc., Edison, NJ
(3) Cremophor RH 20, BASF Corp, Florham Park, NJ In other embodiments, the formulation can be a spray or gel. Topical compositions of the present invention can be formulated as an emulsion using water and a surfactant or emulsifying system, along with the liquid formulations discussed above.

Methods of Making the Formulations

The method of making the formulation containing capsaicin and hyaluronic acid includes the preparation of hyaluronic acid and capsaicin solutions followed by the blending of these solutions to produce the formulation. Typically, the preparation of the hyaluronic acid water solution (composed of a mixture containing 70 wt. % hyaluronic acid with a molecular weight ~11 kDaltons, and 30 wt. % hyaluronic acid with a molecular weight of ~1,000 kDaltons, was added to an alcohol mixture solution containing 0.25 wt. % to 10 wt. % capsaicin dissolved in solublizing (penetrating) agents consisting of ethyl alcohol, propylene glycol, and polyoxy 40 hydrogenated castor oil or PS80 (balance water). Adjusting the relative percentages of the hyaluronic acid molecular weights and surfactant composition resulted in variation of viscosity of the mixture. Example 1 provides details of the preparation of a 2 wt. % capsaicin HA formulation. Methods of making other capsaicinoid formulations are similar to the above.

Methods of Using the Formulations

Pain

The compositions of the present invention discussed above can be used for treating various conditions associated with pain by attenuating pain at a specific site. The components of the formulations are typically administered concomitantly. Examples of conditions to be treated include, but are not limited to, nociceptive pain (pain transmitted across intact neuronal pathways), neuropathic pain (pain caused by damage to neural structures), pain from nerve injury (neuromas and neuromas in continuity), pain from neuralgia (pain originating from disease and/or inflammation of nerves), pain from myalgias (pain originating from disease and/or inflammation of muscle), pain associated with painful trigger points, pain from tumors in soft tissues, pain associated with neurotransmitter-dysregulation syndromes (disruptions in quantity/quality of neurotransmitter molecules associated with signal transmission in normal nerves) and pain associated with orthopedic disorders such as conditions of the foot, knee, hip, spine, shoulders, elbow, hand, head and neck.

Neuropathic pain generally involves abnormalities in the nerve itself, such as degeneration of the axon or sheath. For example, in certain neuropathies the cells of the myelin sheath and/or Schwann cells may be dysfunctional, degenerative and may die, while the axon remains unaffected. Alternatively, in certain neuropathies just the axon is disturbed, and in certain neuropathies the axons and cells of the myelin sheath and/or Schwann cells are involved. Neuropathies may also be distinguished by the process by which they occur and their location (e.g. arising in the spinal cord and extending outward or vice versa). Direct injury to the nerves as well as many systemic diseases can produce this condition including AIDS/HIV, Herpes Zoster, syphilis, diabetes, and various autoimmune diseases. Neuropathic pain is often described as burning, or shooting type of pain, or tingling or itching pain and may be unrelenting in its intensity and even more debilitating than the initial injury or the disease process that induced it.

The receptors involved in pain detection are aptly enough referred to as nociceptor-receptors for noxious stimuli. These nociceptors are free nerve endings that terminate just below the skin as to detect cutaneous pain. Nociceptors are also located in tendons and joints, for detection of somatic pain and in body organs to detect visceral pain. Pain receptors are very numerous in the skin, hence pain detection here is well defined and the source of pain can be easily localized. In tendons, joints, and body organs the pain receptors are fewer. The source of pain therefore is not readily localized. Apparently, the number of nociceptors also influences the duration of the pain felt. Cutaneous pain typically is of short duration, but may be reactivated upon new impacts, while somatic and visceral pain is of longer duration. It is important to note that almost all body tissue is equipped with nociceptors. As explained above, this is an important fact, as pain has primary warning functions. Nociceptive pain preferably includes, but is not limited to post-operative pain, cluster headaches, dental pain, surgical pain, pain resulting from severe burns, postpartum pain, angina, genitor-urinary tract pain, pain associated with sports injuries (tendonitis, bursitis, etc.) and pain associated with joint degeneration and cystitis.

Topical preparations of the compositions of the present invention find use as a topical therapy for a variety of skin disorders that involve pain and itching, such as postherpetic neuralgia, diabetic neuropathy, psoriasis, cluster headache, postmastectomy pain syndrome, rhinopathy, oral mucositis, cutaneous allergy, detrusor hyperreflexia, loin pain/hematuria syndrome, neck pain, amputation stump pain, reflex sympathetic dystrophy, pain due to skin tumor and arthritis, including rheumatoid arthritis, osteoarthritis, diabetic neuropathy, psoriasis, pruritus (itching), cluster headache, post-surgical pain, tendonitis, oral pain, and pain caused by injury, amongst others. The formulations can be used to relieve aches and pains of muscles and joints.

In addition, the preparations of the present invention also find use in topical therapy for: sciatica, fibromyalgia, gout, shingles, eczema, cutaneous allergy conditions, cutaneous inflammatory conditions, cutaneous microbial/fungal infections, trigeminal neuralgia, sinus and nasal congestion, sinus pressure, sinusitis, rhinitis, allergic rhinitis, hyperreactive rhinopathy, nasal polyps, nasal obstruction, sinus infection, dry eye syndrome, chronically dry eyes, anal/genital itch, perianal disease, brachioradial puritus, hemorrhoids, onychomycosis, aural stimulation for non-obstructive dysphagia to improve swallowing function, tinnitus, migraines, dandruff and hair growth.

As used herein, a "therapeutically effective amount" refers to the quantity or dose of an agent to produce a clinically desired result such as a biological or chemical response, or reduction or elimination of a symptom of a disease or condition, e.g. reduction in or elimination of pain
Administration
Topical The compositions of the present invention can be used topically by applying over an area to be treated. A typical method of use is to apply or rub the formulation over the entire area, until the formulation disappears, and use about 1 to 3 or 4 times daily. Additionally, the amount of formulation used can be gradually increased with each successive application. Topical administration can continue for 1-7 days, weeks, or months.

When combined with ingredients disclosed herein, the amount of capsaicinoid (e.g. trans-capsaicin) in the topical preparation can be from 0.075-30 wt. %, 0.2 wt. % to 30 wt. %, between 1 wt. % and 20 wt. %, e.g. 1 wt. %, 5 wt. %, 10 wt. %, and 20 wt. %.

In certain embodiments, the administration of a TRPV1 selective agonist, such as capsaicin, formulations at the discrete site provides pain attenuation or pain relief for at least about 48 hours to about 16 weeks.

Several methods are available for the dispensing of the capsaicin formulations on the skin's surface. TRPV1 selective agonist containing formulation can be applied by physical means including applicator pads, swabs, or other devices intended to apply the formulations in a thin film such as roller bottles, felt tip or sponge tip applicators.
Roller Bottles For liquids formulations, dispensers can include bottles with a constriction to facilitate fluid droplet application to the skin. Especially advantageous for capsaicin containing liquid formulations are tubes and/or bottles with a sponge or a 'roll on' applicator.

Roll on bottles (also referred to as roller bottles) are especially advantageous. The roll on bottle greatly simplifies the dispensing of the fluid on the skin's surface. No finger rubbing or Q-tip application is required. The movement of the roller ball on the skin massages the fluid into the skin.

The roll on bottle has a plastic, glass or metal roll on ball and glass or suitable plastic housing. As the ball rolls it picks up the solution and applies it to the skin's surface. The caps of roll on bottles may contain a special ring on the inner side. This ring presses on the ball when the cap is tightly shut. The pressure on the ball prevents leakage of the product.

After filling the bottles, the roll on housing and ball are fitted into the mouth of the bottle. The roll on housing and ball is fitted by pushing the housing into the mouth of the bottle.

Precise control over where the formulation is applied important. The roller-ball provides a more precise control where the formulation is to be applied, to avoid contact with eyes, contact lenses, tender skin, clothing, etc. The "roll on bottle" minimizes the likelihood of causing lip and/or eye burning since finger application is not required to spread a film of the capsaicin solution on the body.

The roll on bottle configuration allows the TRPV1 selective agonist compositions to be applied as a thin homogeneous film. Generally, the application of a thin film formulation is rapidly absorbed into the skin's surface following application. In several embodiments, substantially complete disappearance of the film is complete within 15 minutes following application, and more usually within 10 minutes, or with some embodiments, even less than 5 minutes after application.
Kits The invention also includes kits comprising a liquid TRPV1 selective agonist composition, and a sustained release agent and surfactant, and a non-occlusive applicator device. The kit can also include a cleaning solution for removal of residual TRPV1 selective agonist such as polyethylene glycol.

The present invention will be further understood after careful consideration is given to the following non-limiting examples thereof.

EXAMPLES

Example 1

Preparation of 100 Grams of "2% Cap-HA Form 2" Topical Formulation
Ingredients:
  2 grams of Trans-Capsaicin Powder, Aversion Technologies, Bowie, Md., USP 30
  0.15 grams of Sodium Hyaluronic Acid Powder, Making Cosmetics Inc., Snoqualmie, Wash.
  0.35 grams of Sodium Hyaluronic Acid (SLMW) Powder, Making Cosmetics Inc., Snoqualmie, Wash.
  20 grams of Ethyl Alcohol, Graves Grain Alcohol, 190 Proof
  10 grams of DGME (Ethoxydiglycol), Lotioncrafter Inc., Eastsound, Wash.
  10 grams of Propylene Glycol, Lotioncrafter Inc., Eastsound, Wash.
  2 grams of Super-refined Polysorbate 80, Croda Inc. Florham Park, N.J.

5 grams of Cremophor RH 20, BASF Corp, Florham Park, N.J.
q.s. Distilled Water

Step I—Preparation of the Hyaluronic Acid Solution

1. Obtain the "tare weight" of a 200 cc Pyrex beaker & add 0.15 grams of Sodium Hyaluronic Acid Powder and 0.35 grams of Sodium Hyaluronic Acid (SLMW) Powder.
2. Slowly add cold (~40° F.) 50 grams of distilled water to the mixture from Step 1 while vigorously stirring, Set aside this mixture for 2 hours while occasionally stirring until all the powder is dissolved and a uniformly optically clear mixture is achieved.

Step II—Preparation of the Capsaicin Solution

1. Add 2 grams of Trans-Capsaicin powder to a 140 cc Pyrex beaker.
2. Add 20 grams of Ethyl Alcohol to the capsaicin powder in Step 1 and slowly stir.
3. Add 10 grams of DGME (Ethoxydiglycol) to the mixture of Step 2 and slowly stir.
4. Add 10 grams of Propylene Glycol to the mixture of Step 3 and slowly stir.
5. Stir the solution mixture from Step 4 and heat on a hot plate to a temperature of ~40° C. until all the trans-capsaicin powder is completely dissolved.
6. Allow the solution from Step 5 to cool to ambient temperatures.

Step III—the Blending of Mixtures from Steps I & II to Produce the "2% Cap-HA Form 2" Formulation 1. Add the liquid contents from STEP II to the HA mixture of STEP I and thoroughly stir.
2. Add 5 grams of Cremophor RH 20 to the mixture from Step 1 and thoroughly stir.
3. Add 5 grams of Super-refined Polysorbate 80 to the mixture from Step 2 and thoroughly stir.
4. The mixture from Step 4 is heated to about 50° C. on a hot plate while stirring.
5. The mixture from Step 4 is cooled to ambient temperatures.
6. The mixture from Step 8 is now ready for subsequent packaging.

Additional Method of Preparation of 100 Grams of the "2% Cap-HA" Topical Formulations
Ingredients:
Trans-Capsaicin Powder, CAS #404-86-4, Formosa Labs, Taoyuan, Taiwan
Sodium Hyaluronic Acid Powder (~1,000 kDa), Making Cosmetics Inc., Snoqualmie, Wash.
Sodium Hyaluronic Acid (SLMW) Powder, Making Cosmetics Inc., Snoqualmie, Wash.
Ethyl Alcohol, Graves Grain Alcohol, 190 Proof
DGME (Ethoxydiglycol), Lotioncrafter Inc., Eastsound, Wash.
Propylene Glycol, Lotioncrafter Inc., Eastsound, Wash.
Polysorbate 80, Croda Inc. Florham Park, N.J.
Cremophor RH 20, BASF Corp, Florham Park, N.J.
Distilled Water Step I—Preparation of the Hyaluronic Acid Solution
1. To a "tared weight" 500 cc Pyrex beaker add 1.95 grams of Sodium Hyaluronic Acid Powder (~1,000 kDa) and 1.05 grams of Sodium Hyaluronic Acid (SLMW, ~20 kDa) Powder.
2. Slowly add 297 grams of ~40° F. distilled water to the beaker from Step 1 with stirring at nominally 500 rpm for nominally 5 minutes. Set this mixture aside for at least 2 hours and occasionally stir until all the powder is dissolved and a uniformly optically clear solution is achieved.

Step II—Preparation of the Capsaicin Solution
1. To a "tared weight" 140 cc Pyrex beaker add 2 grams of Trans-Capsaicin powder.
2. Add 20 grams of Ethyl Alcohol to the capsaicin powder in Step 1 and slowly stir at about 50 rpm with a spatula.
3. Add 10 grams of DGME (Ethoxydiglycol) to the mixture of Step 2 and slowly stir at about 50 rpm with a spatula.
4. Add 10 grams of Propylene Glycol to the mixture of Step 3 and slowly stir at about 50 rpm with a spatula.
5. Add 7 grams of surfactant (such as Polysorbate-80 or Cremophor RH 20) to the mixture of Step 4 and slowly stir at about 50 rpm with a spatula.
6. Stir the solution mixture from Step 5 at about 50 rpm with a spatula while heating on a hot plate to a temperature of ~50° C. until a uniform solution is achieved.
7. Allow the solution from Step 6 to cool to ambient temperature.

Step II—the Blending of Mixtures from Steps I & II to Produce the "2% Cap-HA" Formulation.
1. Slowly add 51 grams of the HA mixture of STEP I to the Capsaicin Solution of STEP II while stirring at about 50 rpm with a spatula.
2. Stir the solution mixture from Step 1 at about 50 rpm with a spatula while heating on a hot plate to a temperature of ~50° C. until a uniform solution is achieved.
3. Allow the solution from Step 6 to cool to ambient temperature.
4. The solution from Step 3 is now ready for subsequent packaging and use.

Example 2

Topical Application of the 0.25% Capsaicin-HA Formulations

This study assessed the tolerability of four topical capsaicin formulations by recording burning sensations and skin irritation on the right and left thigh of a 59-year old male of normal health. The formulations were applied with a rollerball applicator.

TABLE 4

Capsaicin Test Formulations

| Ingredients | 0.15% M/A | [1] 0.25% Cap Form-2 | [2] 0.25% Cap-HA Form-2 | CapZaicin No-Fuss Applicator (Walgreens) |
|---|---|---|---|---|
| Capsaicin | 0.15 | 0.25 | 0.25 | 0.15 |
| Methyl Salicylate | 50 | — | — | — |
| Camphor | 11 | — | — | — |
| Liquefied Phenol | 0.5 | — | — | — |
| Ethyl Alcohol (Grain alcohol) | 23.35 | 20 | 20 | — |
| DGME | — | 10 | 10 | — |
| Propylene Glycol (PG) | — | 10 | 10 | — |

TABLE 4-continued

Capsaicin Test Formulations

| Ingredients | 0.15% M/A | (1) 0.25% Cap Form-2 | (2) 0.25% Cap-HA Form-2 | CapZaicin No-Fuss Applicator (Walgreens) |
|---|---|---|---|---|
| Cremophor RH-40 | — | — | 0.5 | — |
| Hyaluronic Acid ~1,000K Daltons | — | — | 0.15 | — |
| Hyaluronic Acid ~20K Daltons | — | — | 0.35 | — |
| Distilled Water | — | 59.75 | 58.75 | — |
| Other | 15% Menthol | — | — | Carbomer, Glycerin, PG, SD Alcohol (35%), Triethanolamine, Water |

Note:
(1)Formulation No. 1 in Table 3.
(2) Formulation No. 2 in Table 3.

Formulation Application

Each formulation was applied to an area measuring 25 square centimeters (5×5 cm) of skin located on the dorsal thigh. Each formulation was randomly assigned to either the right or left thigh. The application of the formulation involved a non-overlapping serpentine pass of the roller ball or applicator over the skin area that moistened the skin and resulted in a thin film of solution.

The subject evaluated tolerability prior to dosing, one minute after dosing, at 20 minutes and 40 minutes post-dose and at 2 hours after taking a hot shower. Burning was quantified on a 0-10 Numeric Rating Scale using the Wong-Baker faces as a guide. Skin irritation was quantified using a standard 0 to 7 rating scale Burn Rating Scale.

The subject rated burning pain for each site of formulation application, using the following 0 to 10 numeric rating scale, with the Wong-Baker faces scale as a guideline.

BRIEF DESCRIPTION OF DRAWING(S)

The FIGURE shows an exemplary 0 to 10 numeric rating scale.

Skin Irritation Scale

Skin Irritation was Quantified by the Subject Using the Following Definitions:

0=no evidence of irritation

1=minimal erythema, barely perceptible

2=definite erythema, readily visible; minimal edema or minimal papular response

3=erythema and papules

4=definite edema

5=erythema, edema, and papules

6=vesicular eruption

7=strong reaction spreading beyond test results

Results

There was no burning or signs of skin irritation at any of the test sites of skin prior to application of the formulations.

TABLE 5

Burning & Erythema Post Application Measurements For 4 Topical Capsaicin Formulations

| Test Formulations | 1 minute post application | | 20 minutes post application | | 40 minutes post application | | After Hot Shower 2 hours post application | |
|---|---|---|---|---|---|---|---|---|
| | Burning | Erythema | Burning | Erythema | Burning | Erythema | Burning | Erythema |
| 0.15% M/A | 2 | 0 | 2 | 0 | 0 | 0 | 3 | 0 |
| (1)0.25% Cap Form 2 | 3 | 0 | 2 | 0 | 0 | 0 | 6 | 2 very red |
| (2) 0.25% Cap-HA Form 2 | 0 | 0 | 0 | 0 | 0 | 0 | 0 | 0 |
| (3)CapZaicin 0.15% | 2 | 0 | 1 | 0 | 0 | 0 | 3 | 1 red |

Note:
(1)Formulation #1 in Table 3
(2) Formulation #2 in Table 3
(3)Composition: Capsaicin, 0.15 wt. %; Carbomer, Glycerin, PG, SD Alcohol (35%), Triethanolamine, Water

CONCLUSIONS

The 0.15% M/A formulation demonstrated tolerability comparable to that of CapZaicin. Burning scores were identical at 1 minute and 40 minutes post application; however at 20 minutes post application the 0.15% M/A formulation was 1 unit higher in scored burning. Skin irritation scores were identical at 1 minute, 20 minutes and 40 minutes post application; however CapZaicin induced skin reddening following a hot shower 2 hours post application whereas the 0.15% M/A formulation did not induce skin irritation.

The addition of 1% hyaluronic acid dramatically reduced the burning sensation and skin irritation induced by a 0.25% capsaicin aqueous formulation containing ethoxydiglycol and propylene glycol as penetration enhancers.

Example 3

Topical Application of the 0.25% Capsaicin-HA Formulations

A group of 2 adult males and 2 adult females of normal health and ranging in ages from 35 to 55 applied multiple topical application of 4 formulations from 3.7 ml roller-ball applicators as noted in TABLE 6. The subjects noted that the 0.25 wt. % HA/capsaicin formulation was the most tolerable in term of the burning and erythema ratings. The average burning and erythema ratings for the 4 subjects are summarized in TABLE 6.

at time of reading both were at a 1. This quickly reached a zero within 30 minutes of washoff.

B) 2% Cap-HA Form 3 (Formulation 3 in Table 3)—Initially this application site showed no noticeable sensitivity. No irritation/erythema throughout the timeframe. It is important to note there was what could be

TABLE 6

Burning & Erythema Post Application Measurements
For 4 Topical Capsaicin Formulations
(Average of 4 Subjects)

| Test Formulations | 1 minute post application | | 20 minutes post application | | 40 minutes post application | | After Hot Shower 2 hours post application | |
|---|---|---|---|---|---|---|---|---|
| | Burning | Erythema | Burning | Erythema | Burning | Erythema | Burning | Erythema |
| 0.15% M/A | 0.2 | 0 | 2.5 | 0 | 1.2 | 0.3 | 4.7 | 1 |
| [1] 0.25% Cap Form 2 | 0.8 | 0 | 1.6 | 0.5 | 1.3 | 0.5 | 4.0 | 2.6 |
| [2] 0.25% Cap-HA Form 2 | 0.3 | 0 | 0.6 | 0.3 | 0.6 | 0.5 | 2.3 | 0.9 |
| [3] CAPSAICIN 0.15% | 0.6 | 0 | 1.7 | 0.5 | 1.3 | 1.0 | 3.8 | 1.3 |

Note:
[1] Formulation #1 in Table 3
[2] Formulation #2 in Table 3
[3] Composition: Capsaicin, 0.15 wt.%; Carbomer, Glycerin, PG, SD Alcohol (35%), Triethanolamine, Water Example 4

Topical Application of the 2% Capsaicin-HA Formulations

A 40 year old female of normal health applied multiple topical application of 2% trans-capsaicin formulations as noted in Table 3 on her forearm with a 3.7 ml roller-ball applicator. Burning sensations were rated on a scale of 0-10. Erythema (reddening) was rates on a scale of 0-10. (0 no erythema). Erythema (reddening) was rated on a scale of 0-10. The subject experienced the absence of both burning and erythema for both the 2% Cap-HA Form 2 and 2% Cap-HA Form 3 formulations. Burning and stinging recordings for the 2% M/A formulation of <3 were experienced for 60 minutes post application time frame. Details of the subject's comments relating to the topical application of the 3 formulations are summarized in the Tables below.

A) 2% Cap-HA Form 2 (Formulation 3 in Table 3)—Initially this application site showed no noticeable sensitivity. No irritation/erythema throughout the test. There was no burning sensation or redness prior to the 60 minute timepoint. Upon washing of the product in hot water, a slight itching sensation and erythema occurred, described as a pleasant warming of the area 18 hours later when showering. This warming dissipated within 30 minutes post shower.

C) [1] 2% MA—Initially this application site showed barely noticeable sensitivity, described as an itching sensation. There was mild irritation/erythema upon initial application. The burning sensation increased to a 2.5 at the 10 minute mark. The burning sensation gradually dissipated to a mild itching. The burning sensation increased to a 3 immediately upon exposure to hot water and remained at this level for 10 minutes following. Pain then gradually decreased to 0 over the course of 40 minutes following wash off. No erythema or pain was noticeable until a shower the next day. At which time there was a light erythema and a mild burning characterized as a 3. This pain dissipated within 30 minutes.

Note: ([1]) Composition: Capsaicin. 2 wt. %: Methyl Salicylate, 50 wt. %: Menthol, 15 wt. %: Camphor. 11 wt. %: Ethyl Alcohol. 19.5 wt. %: Phenol 1.35 wt. %. Water, 1.15 wt.

TABLE 7

Burning & Erythema Post Application Measurements

| Test Formulations | 1 minute post application | | 10 minutes post application | | 20 minutes post application | | 30 minutes post application | | 45 minutes post application | | 60 minutes post application | |
|---|---|---|---|---|---|---|---|---|---|---|---|---|
| | Burning | Erythema | Burning | Erythema | Burning | Erythema | Burning | Irritation | Burning | Erythema | Burning | Erythema |
| [1] 2% Cap-HA Form 2 | 0 | 0 | 0 | 0 | 0 | 0 | 0 | 0 | 0 | 0 | 0 | 0 |
| [2] 2% Cap-HA Form 3 | 0 | 0 | 0 | 0 | 0 | 0 | 0 | 0 | 0 | 0 | 0 | 0 |
| 2% M/A | 1.5 | 1.5 | 2.5 | 2 | 2 | 3 | 2 | 3 | 2 | 3 | 2 | 3 |

Note:
[1] Formulation #3 in Table 3
[2] Formulation #4 in Table 3
[3] Composition: Capsaicin, 2 wt. %: Methyl Salicylate, 50 wt. %; Menthol, 15 wt. %; Camphor, 11 wt. %; Ethyl Alcohol, 19.5 wt. %; Phenol 1.35 wt. %, Water, 1.15 wt.

TABLE 8

Burning & Erythema Post Application Measurements

| Test Formulations | Immediate Post Wash-Off (with hot water) | | 18 hours later during Shower | |
|---|---|---|---|---|
| | Burning | Erythema | Burning | Erythema |
| [1] 2% Cap-HA Form 2 | 1 | 0 | 1 | 0.5 |
| [2] 2% Cap-HA Form 3 | 0 | 0 | 1 | 0 |
| [3] 2% M/A | 3 | 3.5 | 3 | 0.5 |

Note:
[1] Formulation #3 in Table 3
[2] Formulation #4 in Table 3
[3] Composition: Capsaicin, 2 wt. %; Methyl Salicylate, 50 wt. %; Menthol, 15 wt. %; Camphor, 11 wt. %; Ethyl Alcohol, 19.5 wt. %; Phenol 1.35 wt. %, Water, 1.15 wt.

Example 5

Topical Application of the 2% Capsaicin-HA Formulations

A 50-year old male of normal health applied a single topical application of three 2 wt. % trans-capsaicin formulations via a roller ball applicator. The burning and erythema ratings are summarized in Table 9. Both formulations containing HA had similar burning and erythema ratings for the 60 minute post application duration as noted in Table 9. The subject rated the 2 wt. % M/A formulation as slightly more burning and more irritating than the HA formulations. All levels of burning and erythema were considered to be well within the "tolerable" level for topical use in the subject's opinion.

TABLE 9

Burning & Erythema Post Application Measurements

| Test Formulations | 1 minute post application | | 10 minutes post application | | 20 minutes post application | | 30 minutes post application | | 45 minutes post application | | 60 minutes post application | |
|---|---|---|---|---|---|---|---|---|---|---|---|---|
| | Burning | Erythema | Burning | Erythema | Burning | Erythema | Burning | Irritation | Burning | Erythema | Burning | Erythema |
| [1] 2% Cap-HA Form 2 | 1.5 | 0 | 2 | 0 | 2.5 | 0.5 | 2.5 | 0.5 | 2.5 | 0.5 | 2.0 | 1 |
| [2] 2% Cap-HA Form 3 | 1.5 | 0 | 2 | 0 | 2.5 | 0.5 | 2.5 | 0.5 | 2.5 | 0.5 | 2.0 | 1 |
| 2% M/A | 1 | 0 | 2.5 | 0.5 | 3 | 1 | 3.5 | 1 | 3.0 | 0.5 | 2.5 | 1 |

Note:
[1] Formulation #3 in Table 3
[2] Formulation #4 in Table 3
[3] Composition: Capsaicin, 2 wt. %; Methyl Salicylate, 50 wt. %; Menthol, 1.5 wt. %; Camphor, 11 wt. %; Ethyl Alcohol, 19.5 wt. %; Phenol 1.35 wt. %, Water, 1.15 wt.

Example 6

Topical Application of the 5% and 10% Capsaicin Formulations

A 79 year old male took part in an evaluation of both the 5 wt. % and 10 wt. % capsaicin-HA to evaluate the burning and erythema effect of capsaicin. The burning effect was rated on a scale of (0-10) and at the same time erythema reddening was also determined by eye on a scale of (1-5).

Application of the 5 wt. % capsaicin-HA formulation via 3.7 ml roller-ball bottle was undertaken to achieve an initial dosing on a 25 cm$^2$ (5 cm×5 cm) area of skin on his left arm, 20 cm below the elbow joint on the underside of his left arm. Several passes of the roller-ball were undertaken to the entire 25 cm application area.

Similarly, application of 10 wt. % capsaicin-HA formulation via 3.7 ml roller-ball bottle was undertaken to achieve an initial dosing on a 25 cm$^2$ (5 cm×5 cm) area of skin on his left arm, 20 cm above the elbow joint on the upper side of the right arm. Several passes of the roller-ball were applied to the 25 cm$^2$ application area.

The observed burning and erythema results are summarized in Tables 10 and 11. The subject noted a gradual increase in the burning sensation to a 3 level for the 5 wt. % capsaicin and a level 2.5 for the 10 wt. % capsaicin formulation at the 20 minute mark followed by a gradual decrease to zero after 60 minutes. The subject noted a slight itching that lasted for about 5 to 15 minutes after fluid application.

In both cases the level of burning for both the 5 wt. % and 10 wt. % Capsaicin/HA formulation were well tolerated.

TABLE 10

Burning & Erythema Post Application Measurements

| Test Formulations | 1 minute post application | | 10 minutes post application | | 20 minutes post application | | 30 minutes post application | | 45 minutes post application | | 60 minutes post application | |
|---|---|---|---|---|---|---|---|---|---|---|---|---|
| | Burning | Erythema | Burning | Erythema | Burning | Erythema | Burning | Irritation | Burning | Erythema | Burning | Erythema |
| (1) 5% Cap-HA Form 2 | 0 | 0 | (3) 2 | 0 | 3.0 | 0 | 1.5 | 0 | 0.5 | 0.5 | 0 | 0 |
| (2) 10% Cap-HA Form 3 | 0 | 0 | (3) 2.50 | 0 | 2.5 | 0.5 | 2.0 | 0 | 1 | 0 | 0 | 0 |

Note:
(1) Formulation #5 in Table 3
(2) Formulation #6 in Table 3
(3) Slight itching experienced

TABLE 11

Burning & Erythema Post Application Measurements

| Test Formulations | Immediate Post Wash-Off (with hot water) | | 18 hours later during Shower | |
|---|---|---|---|---|
| | Burning | Erythema | Burning | Erythema |
| (1) 5% Cap-HA Form 2 | 1 | 0.5 | 1 | 0.5 |
| (2) 10% Cap-HA Form 3 | 2 | 0.5 | 0 | 0 |

Note:
(1) Formulation #5 in Table 3
(2) Formulation #6 in Table 3

Example 7

Topical Application of the 5% and 10% Capsaicin-HA Formulations

A 71-year old female of normal health applied a single topical application of the 5 wt. % capsaicin-HA formulation to her left forearm and the 10 wt. % capsaicin-HA formulation to her right forearm in a manner similar to that described in Example 6. The observed burning and erythema results are summarized in TABLES 12 and 13. The level of burning for both the 5 wt. % and 10 wt. % Capsaicin/HA formulation were well tolerated.

TABLE 12

Burning & Erythema Post Application Measurements

| Test Formulations | 1 minute post application | | 10 minutes post application | | 20 minutes post application | | 30 minutes post application | | 45 minutes post application | | 60 minutes post application | |
|---|---|---|---|---|---|---|---|---|---|---|---|---|
| | Burning | Erythema | Burning | Erythema | Burning | Erythema | Burning | Irritation | Burning | Erythema | Burning | Erythema |
| (1) 5% Cap-HA Form 2 | 0 | 0 | (3) 1 | 0.5 | 3.0 | 0.5 | 2.0 | 0.5 | 0.5 | 0 | 0 | 0 |
| (2) 10% Cap-HA Form 3 | 0 | 0 | (3) 3.0 | 1 | 2.5 | 1 | 2.0 | 0 | 1 | 0 | 0.5 | 0 |

Note:
(1) Similar to Formulation #5 in Table 3
(2) Similar to Formulation #6 in Table 3
(3) Slight itching experienced

TABLE 13

Burning & Erythema Post Application Measurements

| Test Formulations | Immediate Post Wash-Off (with hot water) | | 18 hours later during Shower | |
|---|---|---|---|---|
| | Burning | Erythema | Burning | Erythema |
| (1) 5% Cap-HA Form 2 | 3 | 1 | 2 | 1 |
| (2) 10% Cap-HA Form 3 | 2 | 1 | 2 | 0 |

Note:
(1) Similar to Formulation #5 in Table 3
(2) Similar to Formulation #6 in Table 3

Example 8

Topical Application of 2%. 5% and 10% CAPSAICIN-HA Formulation with PS80 to Rats A small rat study was conducted utilizing the capsaicin-HA formulations below:

2%, 5%, and 10% CAPSAICIN-HA FORMULATIONS
(Optically Clear Single Phase Formulations)

| INGREDIENTS | 2 wt. % HA-Cap | 5 wt. % HA-Cap | 10 wt. % HA-Cap |
|---|---|---|---|
| CAPSAICIN (Formosa) | 2 | 5 | 10 |
| POLYSORBATE 80 (Super Refined - Croda) | 7 | 10 | 13 |
| ETHYL ALCOHOL (Grain Alcohol) | 20 | 20 | 20 |
| ETHOXYDIGLYCOL METHYL ETHER (DGME) | 10 | 10 | 10 |
| PROPYLENE GLYCOL | 10 | 10 | 10 |
| (1)HA (~1,000K Daltons) | 0.17 | 0.17 | 0.12 |
| (1)HA SLMW (~20K Daltons) | 0.33 | 0.33 | 0.25 |
| (1)DISTILLED WATER | 50.50 | 44.50 | 36.63 |
| TOTAL | 100 | 100 | 100 |

A single administration of the 2% and 5% capsaicin formulations for 30 minutes was tolerated in the rats. A single administration of the 10% capsaicin formulation for 30 minutes was not well tolerated in the rats.

Example 9

Topical Application of 10% CAPSAICIN-HA Formulation with PS80 to a Human

A 53-year old male of normal health applied a single topical application of 10% trans-capsaicin hyaluronic acid (HA) PS80 solution for 120 minutes prior to washing off. This formulation was formulated with PS80 as the surfactant. Composition of the formulation is shown in the following table.

Composition of the 10% HA-CAPSAICIN FORMULATION

| INGREDIENTS | wt. % |
|---|---|
| CAPSAICIN (Formosa) | 10 |
| POLYSORBATE 80 (PS80) (Super Refined - Croda) | 13 |
| ETHYL ALCOHOL (Grain Alcohol) | 20 |
| ETHOXYDIGLYCOL METHYL ETHER (DGME) | 10 |
| PROPYLENE GLYCOL | 10 |
| HA (~1,000K Daltons) | 0.12 |
| HA SLMW (~20K Daltons) | 0.25 |
| DISTILLED WATER | 36.63 |
| TOTAL | 100 |

Application of formulation via 10 mg roller-ball bottle was undertaken to achieve a liberal "glistening" dose over a 15 in (5 inch×3 inch) area of skin on right knee covering half the knee cap and the space just above the knee cap. Several passes of the roller-ball were undertaken to the entire application area to achieve this liberal dosing of formulation.

Rating of stinging/burning (S&B) and Redness (Erythema) are shown in the table below as a function of time following topical application.

| Minutes | S&B Scale 0-10 | Erythema Scale 0-5 |
|---|---|---|
| 2 | 1 | 0 |
| 5 | 1.5 | .5 |
| 10 | 2 | 1 |
| 20 | 2 | 1.5 |
| 30 | 2 | 1.5 |
| 40 | 2.5 | 1.5 |
| 60 | 2 | 2 |
| 80 | 1 | 1.5 |
| 90 | 1 | 1 |
| 100 | 0.5 | 0.5 |
| 120 | 0.5 | 0.5 |

In the table above, the S&B Scale of 0 to 10 is a representation of "stinging and burning" where a zero represents an absence of any S&B, a 1 is a slight S&B, a 5 is an intolerable amount of S&B and a 10 is the worst pain imaginable. Likewise, the 0 to 5 Erythema scale represents the amount of reddening visually observed where a zero is an absence of reddening, a 1 indicates slight reddening of the skin, a 3 indicates a dark red color and a 5 is purple.

Overall subject observed a gradual onset of a slight, but very tolerable, burning and stinging sensation over the first 40 minutes following application, followed by a gradual decrease after that point until the 120 minute mark, at which time a very slight S&B sensation still remained. In more detail, a slight S&B sensation rated at a 1 was felt after only 2 minutes, and rose to a 2 rating after 10 minutes. Maximum S&B rated at a 2.5 (on a scale of 0-10) was observed after 40 minutes. The S&B sensation slowly and gradually increased prior to the 40 minute mark. This maximum of 2.5 rated S&B sensation was observed to be quite tolerable at its peak, and then and gradually dissipated beyond the 40-minute mark. From the 40-minute mark on the subject observed a gradual reduction of S&B sensation until the 100 minute mark, at which time the S&B level was observed as a very slight 0.5 rating (on a scale of 1-10). This very slight 0.5 S&B rating continued until the end of the 120 minute period recorded. All levels of irritation were considered to be well within a "tolerable" level for topical use in subject's opinion.

In addition, reddening (erythema) and reduction of reddening of the entire 50 cm$^2$ application area was observed over the initial 120 minute period following application. Subject observed a reddening rated at a 0.5 (on a scale of 1-5) after 5 minutes, to a rating of 1.0 after 10 minutes, and a rating of 1.5 after 20 minutes. This reddening rating of 1.5 was the maximum level observed and lasted from the 20 minute mark until the 40 minute mark. Reddening gradually lessened after the 40-minute mark and was down to an S&B rating of 0.5 after 100 minutes. This slight reddening of 0.5 rating was still observed at the end of the 120 minute period recorded. Reddening was uniform and no blotching or other form of inconsistent effect was observed. The area of reddening did not expand beyond the area of application: only skin area directly treated with the formulation had erythema associated with it. Skin did not become more sensitive during the 120 minute application of the formulation.

Example 10

Topical Application of 10% CAPSAICIN-HA Formulation with PS80 to a Human

A 41-year old female of normal health applied a single topical application of 10% trans-capsaicin hyaluronic acid (HA) PS80 solution for 120 minutes prior to washing off. The composition of this formulation is shown in the following table.

Composition of the 10% HA-CAPSAICIN FORMULATION

| INGREDIENTS | wt. % |
|---|---|
| CAPSAICIN (Formosa) | 10 |
| POLYSORBATE 80 (PS80) (Super Refined - Croda) | 13 |
| ETHYL ALCOHOL (Grain Alcohol) | 20 |
| ETHOXYDIGLYCOL METHYL ETHER (DGME) | 10 |
| PROPYLENE GLYCOL | 10 |
| HA (~1,000K Daltons) | 0.12 |
| HA SLMW (~20K Daltons) | 0.25 |
| DISTILLED WATER | 36.63 |
| TOTAL | 100 |

Application of formulation via 10 mg roller-ball bottle was undertaken to achieve a liberal "glistening" initial dosing on a 8 in$^2$ (4 inch×2 inch) area of skin on the inner right forearm. Several passes of the roller-ball were undertaken to the entire application area to achieve this liberal dosing of formulation.

Rating of stinging/burning (S&B) and Redness (Erythema) are shown in the table below as a function of time following topical application.

| Minutes | S&B Scale 0-10 | Erythema Scale 0-5 |
|---|---|---|
| 2 | 0 | 0 |
| 5 | 1 | 1 |
| 10 | 1 | 1 |
| 20 | 1 | 1.5 |
| 30 | 1 | 1.5 |
| 40 | 1 | 1.5 |
| 60 | 1 | 1.5 |
| 80 | 1 | 1.5 |
| 90 | 1 | 1.5 |
| 100 | 0.5 | 0.5 |
| 120 | 0.5 | 0.5 |

In the table above, the S&B Scale of 0 to 10 is a representation of "burning and stinging" where a zero represents an absence of any S&B, a 1 is a slight S&B, a 5 is an intolerable amount of S&B and a 10 is the worst pain imaginable. Likewise, the 0 to 5 Erythema scale represents the amount of reddening visually observed where a zero is an absence of reddening, a 1 indicates slight reddening of the skin, a 3 indicates a dark red color and a 5 is purple.

A slight stinging sensation rated at a 1 was felt after 5 minutes, and stayed steady until the 100 minute mark where it gradually decreased. The maximum S&B rated at a 1 (on a scale of 0-10) was observed through 90 minutes. This 1 rated S&B was observed to be quite tolerable. From the 100-minute mark on, the subject observed a gradual reduction of S&B sensation. The very slight 0.5 S&B continued until the end of the 120 minute period recorded. All levels of irritation were well within a "tolerable" level for topical use in subject's opinion.

In addition, reddening (erythema) and reduction of reddening of the entire application area was observed over the initial 120 minute period following application. Subject observed a reddening rated at a 1 (on a scale of 1-5) after 5 minutes, to a rating of 1.5 after 10 minutes that continued past the 90 minute mark. Reddening gradually lessened after the 100-minute mark and was down to a 0.5 for the duration. This slight reddening of 0.5 rating was still observed at the end of the 120 minute period recorded. Reddening was uniform and no blotching or other form of inconsistent effect was observed. The area of reddening did not expand beyond the area of application: only skin area directly treated with the formulation had erythema associated with it.

Skin did not become more sensitive during the 120 minute application of the formulation.

Example 11

Four Daily Dose Treatments of Osteoarthritis with a 10% Capsaicin-HA Formulation A 59 year old man suffering from severe and advanced osteoarthritis used a 10% capsaicin hyaluronic acid formulation once a day on four successive days for mitigation of osteoarthritis pain. The formulation used contained 10% w/w capsaicin along with hyaluronic acid (HA) and utilized Cremaphore RH40 as a stabilization agent (see Table below). This man was Caucasian, obese with degenerative joint disease (osteoarthritis) especially in the knees, bilaterally, with severe degeneration of medial and lateral meniscus and articular cartilage bilaterally, right greater than left. At the time, pain was marginally controlled with Tramadol 50-100 mg tid, giving partial relief, bringing the pain level down to approximately 4 on the pain scale, with sharp shooting pains that scale up to 8-9.

Efficacy

The subject noted that "After treating my worse knee (right) with the 10% formulation for one hour a day for four days, my pain relief improved to a pain level of 2, making my more troublesome knee the better, most pain free knee. The sharp shooting pains also improved and were much less frequent with the momentary severe pain levels only reaching 5. This change for the better lasts for weeks."

Tolerability

The subject noted that "My stinging/burning sensation while applying the treatment was only a trace, less than 1 by my estimate. The sting/burn only slightly increases in the shower, at most to a 1 on the pain scale. While in the shower there was a mild, manageable cough as I rinsed the treated area, fortunately this was only momentary because the formulation washes away easily, quickly and completely."

Overall Assessment

The subject was very pleased with the results.

Formulation Composition Table

| INGREDIENTS | wt. % |
|---|---|
| CAPSAICIN (Formosa) | 10 |
| CREMOPHOR RH 40 | 12 |
| ETHYL ALCOHOL (Grain Alcohol) | 20 |
| ETHOXYDIGLYCOL (DGME) | 10 |
| PROPYLENE GLYCOL | 10 |
| [1] HYALURONIC ACID AQUEOUS SOLUTION | 38 |
| TOTAL | 100 |

Note:
[1] The Hyaluronic Acid Aqueous Solution contains 0.65 wt. % Hyaluronic Acid SLMW (~20K Daltons), 0.35 wt. % Hyaluronic Acid 1,000K Daltons) and 99 wt. % Distilled Water.

Example 12

Single Dose Pulse Treatment of Osteoarthritis with a 10% Capsaicin-HA Formulation A 79 year old man with a history of moderate to severe Osteoarthritis in multiple joints (successful hip replacement in 2008) used a 10% capsaicin HA formulation several times for mitigation of arthritis pain in both his hip and shoulder joints. The formulation used contained 10% w/w capsaicin along with hyaluronic acid (HA) and utilized Cremaphore RH40 as a stabilization agent (see Table below).

Efficacy:

The subject applied the above mentioned formulation several times on both his left hip and his right shoulder to control osteoarthritis pain. He applied the 10% Capsaicin HA formulation on an "as needed" basis, which on average was estimated to be once every two weeks. When he applied the formulation, he generally left it on for at least one hour prior to washing off. He did not repeat doses on back to back days, but instead applied a single dose, and then waited until the pain returned to apply another dose. When a single dose of this 10% capsaicin formulation with hyaluronic acid was applied, the arthritis pain was completely eliminated in his shoulder joint for approximately two weeks. Similarly, pain was reduced by approximately 80% when applied on his arthritic hip joint, and significant pain did not return to his hip joint for duration of about 2 weeks from a single dose. The average time to return of pain in both joints was approximately 2 weeks. He was very pleased with the convenience of 1 to 2 weeks of pain relief from the capsaicin following each single dose.

Tolerability:

The subject noted that the application of this formulation was very tolerable (not irritating). He observed no burning and stinging (B&S) irritation upon application to his shoulder joint for all applications to his shoulder. When he applied the formulation to his hip joint (avoiding the groin and buttocks areas) the maximum S&B sensation was never greater than a 2 rating on a scale of 0 to 10 (defined as zero meaning no S&B sensation, 5 denoting intolerable pain and 10 representing the worst pain imaginable). Erythema (reddening) was non-existent on his shoulder joint upon application, and was estimated at a rating or 1.5 (on a scale of 0 to 5) when the formulation was applied to his hip joint (ratings defined as zero representing an absence of reddening, a 3 as dark red and a 5 as purple). In terms of both S&B sensation and erythema, the subject found the formulation to be very tolerable.

Formulation Composition Table

| INGREDIENTS | wt. % |
|---|---|
| CAPSAICIN (Formosa) | 10 |
| CREMOPHOR RH 40 | 12 |
| ETHYL ALCOHOL (Grain Alcohol) | 20 |
| ETHOXYDIGLYCOL (DGME) | 10 |
| PROPYLENE GLYCOL | 10 |
| [1] HYALURONIC ACID AQUEOUS SOLUTION | 38 |
| TOTAL | 100 |

Note:
[1] The Hyaluronic Acid Aqueous Solution contains 0.65 wt. % Hyaluronic Acid SLMW (~20K Daltons), 0.35 wt. % Hyaluronic Acid 1,000K Daltons) and 99 wt. % Distilled Water.

Example 13

Capsaicin—HA formulations containing Analgesics

A 1 wt. % hyaluronic acid water solution composed of a mixture containing 70% Hyaluronic Acid with a molecular weight 20K Daltons and 30% hyaluronic acid with a molecular weight 1,00K Daltons, was added to an alcohol mixture solutions containing 0.25 wt. % and 2.0 wt. % Capsaicin dissolved in 20% ethyl alcohol and 10% propylene glycol and 15 wt. % and 17 wt. % Cremophor™ RH 40, respectively. Optically crystal clear and moderately viscous solutions were formed. Adjusting the relative percentages of hyaluronic acid molecular weights could vary the viscosity of the mixture.

Both the 0.25% wt. % and 2.0 wt. % capsaicin formulations (see Table below) as described in the foregoing paragraphs were applied to an 80 year old male subject's right forearm via a 5 ml roller-ball vial. The applied liquid film dried in a few minutes. Minimal discomfort from burning & stinging was experienced. Significantly, the formulations containing 10 wt. % methyl salicylate were relatively odor free.

CAPSAICIN-ANALGESIC-HA-FORMULATIONS

| INGREDIENTS | FUNCTION | ¼% Cap-HA (wt. %) | 2% Cap-HA (wt. %) |
|---|---|---|---|
| Capsaicin (Formosa) | TRPV1 Agonist | 0.25 | 2 |
| Methyl Salicylate | Analgesic Agent & Penetrant | 10 | 10 |
| Menthol | Cooling Agent & Penetrant | 5 | 5 |
| Camphor | Anesthetic Agent Penetrant | 2 | 2 |
| Cremophor RH 40 | Surfactant & Solubilizer | 15 | 17 |
| Ethyl Alcohol (Grain Alcohol) | Solubilizer & Penetrant | 20 | 20 |
| Diethylene Glycol Monoethyl Ether (DGME) | Solubilizer & Penetrant | 0 | 0 |
| Propylene Glycol | Solubilizer & Penetrant | 10 | 10 |
| [1] Hyaluronic Acid Aqueous Solution | Moisturizer & Humectant | 37.75 | 34 |
| TOTAL | | 100 | 100 |

Note:
[1] The Hyaluronic Acid Aqueous Solution contains 0.65 wt. % Hyaluronic Acid SLMW (~20K Daltons), 0.35 wt. % Hyaluronic Acid 1,000K Daltons) and 99 wt. % Distilled Water.

Example 14

Comparison of Tolerability and Erythema Following Topical Application of Two (2%) Capsaicin HA Formulations: Effect of the Inclusion of Analgesics The purpose of this study was to evaluate tolerability and erythema created by the inclusion of topical analgesics to a capsaicin hyaluronic acid (HA) formulation following topical application. A 53 year old male applied two distinct formulations of 2% capsaicin HA (one formulation with topical analgesics and one without) on a single knee side by side. Burning and stinging (S&B) along with skin redness were quantified following topical application in older to evaluate the tolerability and erythema characteristics singularly and comparatively with the two formulations. The compositions of the two formulations are shown below as Formulation 1 (Capsaicin HA) and Formulation 2 (Capsaicin HA plus Analgesics).

| Formulation 1 Composition Capsaicin HA Formulation | |
| --- | --- |
| INGREDIENTS | wt. % |
| CAPSAICIN (Formosa) | 2 |
| CREMOPHOR RH 40 | 7 |
| ETHYL ALCOHOL (Grain Alcohol) | 20 |
| Diethylene Glycol Monoethyl Ether (DGME) | 10 |
| PROPYLENE GLYCOL | 10 |
| [1] HYALURONIC ACID AQUEOUS SOLUTION | 51 |
| TOTAL | 100 |

| Formulation 2 Composition Capsaicin HA plus Analgesics Formulation | | |
| --- | --- | --- |
| INGREDIENTS | FUNCTION | wt. % |
| Capsaicin (Formosa) | TRPV1 Agonist | 2 |
| Methyl Salicylate | Analgesic & Solvent | 10 |
| Menthol | Analgesic & Cooling | 5 |
| Camphor | Analgesic | 2 |
| Cremophor RH 40 | Surfactant | 17 |
| Ethyl Alcohol (Grain Alcohol) | Solvent | 20 |
| Diethylene Glycol Monoethyl Ether (DGME) | Solvent | 0 |
| Propylene Glycol | Solvent & Humectant | 10 |
| [1] Hyaluronic Acid Aqueous Solution | Moisturizer & Humectant | 34 |
| TOTAL | | 100 |

Note:
[1] The Hyaluronic Acid Aqueous Solution contains 0.65 wt. % Hyaluronic Acid SLMW (~20K Daltons), 035 wt. % Hyaluronic Acid 1,000K Daltons) and 99 wt. % Distilled Water.

Formulation 1 below is a 2% capsaicin HA formulation. Formulation 2 below consists of 2% Capsaicin HA alone with several well-known natural analgesic compounds. Tolerability (S&B) was assessed using a scale of 0 to 10, where a zero represents an absence of any S&B, a 1 is a slight S&B, a 5 is an intolerable amount of S&B and a 10 is the worst pain imaginable. Likewise, the 0 to 5 Erythema scale represents the amount of reddening visually observed on the skin where a zero rating is an absence of reddening, a 1 rating indicates slight reddening of the skin, a 3 rating indicates a dark red color, and a 5 is purple.

A 53 year old male applied both formulations at the same time. The two formulations were applied side by side and then Tolerability (S&B) and Erythema (reddening) ratings were taken for each formulation application over a 120 minute period. The ratings are shown in S&B Table and Redness Table below. The tolerability of Formulation 2 (2% Capsaicin HA plus Analgesics) was not only at the extreme low end of the tolerability scales by both measures, but was even lower than Formulation 1 (2% Capsaicin HA) by direct comparison. For Formulation 1, a maximum S&B rating of 2.0 and a maximum Erythema rating of 1.5 were observed by the 20 minute time point. Both ratings gradually decreased to zero by the 90 minute time point. For Formulation 2, a maximum S&B rating of 1.5 was observed at the 30 minute time point, and then gradually decreased to zero by the 90 minute time point. Formulation 2 Erythema maximum was observed by the 20 minute time point at a rating of 0.5 and this rating decreased to zero by the 60 minute time point.

| S&B Table Tolerability Comparisons (Scale 0 to 10) | | |
| --- | --- | --- |
| Elapsed Time of Rating | Formulation #1 Rating | Formulation #2 Rating |
| 2 Minutes | 0.5 | 0 |
| 5 Minutes | 1.0 | 0.5 |
| 10 Minutes | 1.5 | 1.0 |
| 20 Minutes | 2.0 | 1.5 |
| 30 Minutes | 2.0 | 1.0 |
| 45 Minutes | 1.0 | 0.5 |
| 60 Minutes | 0.5 | 0 |
| 90 Minutes | 0 | 0 |
| 120 Minutes | 0 | 0 |

| Redness Table Erythema Comparisons (Scale 0 to 5) | | |
| --- | --- | --- |
| Elapsed Time of Rating | Formulation #1 Rating | Formulation #2 Rating |
| 2 Minutes | 0 | 0 |
| 5 Minutes | 0.5 | 0 |
| 10 Minutes | 1.0 | 0 |
| 20 Minutes | 1.0 | 0.5 |
| 30 Minutes | 1.5 | 0.5 |
| 45 Minutes | 1.0 | 0.5 |
| 60 Minutes | 0.5 | 0 |
| 90 Minutes | 0 | 0 |
| 120 Minutes | 0 | 0 |

Despite containing 2% capsaicin, both formulations were observed to be very tolerable in terms of both the stinging and burning sensation (S&B), as well as visual reddening (Erythema). Furthermore, addition of analgesics to 2% Capsaicin HA (Formulation 2, Capsaicin HA plus Analgesics) resulted in lower ratings of both S&B sensation and erythema relative to 2% Capsaicin HA (Formulation 1, Capsaicin HA).

Example 15

Single Dose Treatment of Back Muscles with a 10% Capsaicin-HA Formulation

A 79 year old man used a 10% capsaicin HA formulation for mitigation of pain in his back due to his back muscles seizing up in spasm and causing intense pain. The formulation used contained 10% w/w capsaicin along with hyaluronic acid (HA) and utilized Cremaphore RH40 as a stabilization agent (see Table below).

Efficacy:

A 79 year old man still with an active lifestyle (and a history of back problems) was playing tennis when his back "went out" while picking up a tennis ball. He collapsed on the court, and any attempt to move caused him intense pain that he rated as an 8 on a scale of 0 to 10 (where zero is an absence of pain and a 10 is the worst pain imaginable). The subject was practically immobilized and lay flat on his back on the tennis court and required assistance to get up and be moved to a bed. He reported that the muscles in his middle and lower back has seized up from an abnormality with a nerve in his back (doctors had previously explained to him). Previously when this problem had occurred he required many days of bed rest to recover. Once in bed, he requested his wife to apply 10% capsaicin and hyaluronic acid (with Cremaphore RH40) formulation over a 12"×12" area on his back where the muscles had seized up in spasm. About 90% of the treatment area consisted of muscle with the spine in the middle. When a single dose of this 10% capsaicin formulation with hyaluronic acid was applied, the pain was eliminated in his back within 20 minutes following application. The muscles in his back had relaxed. The muscle spasms were gone and he began to move around in normal motions without pain over the course of one hour. At the end of two hours, he felt normal and went out and resumed his tennis game. The capsaicin with HA formulation had provided relief that previously had only been achieved from days of bed rest and restricted activity.

Tolerability:

The subject observed the topical application of this formulation to be very tolerable (not irritating). He observed only minor Stinging and Burning (S&B) irritation upon application to his back. When the formulation was applied to the relatively large area on his back he gradually felt a warming sensation grow over the initial 2 to 3 minutes following application. The subject noted this was a comforting sensation. He observed that at its maximum, the Stinging and Burning sensation (S&B) was rated at no more than a 2.5 on a scale of 0 to 10 (defined as zero meaning no S&B sensation, 5 denoting intolerable pain and 10 representing the worst pain imaginable). Erythema (reddening) was present across the entire area of application very evenly, and appeared at its worst to look like a mild sunburn. At its worst, this erythema was estimated at a rating of 1.5 on a scale of 0 to 5: where a zero represents a complete absence of erythema, a 1 is slight reddening, a 3 as dark red and a 5 as purple. In terms of both S&B sensation and erythema, the subject found the formulation to be very tolerable.

| Formulation Composition Table | |
|---|---|
| INGREDIENTS | wt. % |
| CAPSAICIN (Formosa) | 10 |
| CREMOPHOR RH 40 | 12 |
| ETHYL ALCOHOL (Grain Alcohol) | 20 |
| ETHOXYDIGLYCOL (DGME) | 10 |
| PROPYLENE GLYCOL | 10 |
| (1) HYALURONIC ACID AQUEOUS SOLUTION | 38 |
| TOTAL | 100 |

Note:
(1) The Hyaluronic Acid Aqueous Solution contains 0.65 wt. % Hyaluronic Acid SLMW (~20K Daltons), 0.35 wt. % Hyaluronic Acid 1,000K Daltons and 99 wt. % Distilled Water.

Example 16

Tolerability of a 5% Capsaicin-HA Formulation Containing Polysorbate 80 to Knees Afflicted with Osteoarthritis

| Formulation Composition Table | | |
|---|---|---|
| Ingredients | Function | Wt. % |
| Capsaicin | Defunctionalization of TRPV-1 sensory neurons | 5.0 |
| Hyaluronic Acid ~1,000K Daltons | Viscosity enhancer & moisturizing agent | 0.15 |
| Hyaluronic Acid ~11K Daltons | Viscosity enhancer & moisturizing agent | 0.35 |
| Ethyl Alcohol | Solvent | 20 |
| DGME | Solvent & penetration enhancer | 10 |
| Propylene Glycol | Solvent & penetration enhancer | 10 |
| Polysorbate 80 | Surfactant, emulsifier & solubilizing agent | 10 |
| Water | Solvent | q.s. |

A 70 year old man applied a 5% capsaicin HA formulation containing polysorbate 80 (composition shown in table above) to both of his knees afflicted with osteoarthritis. The man experienced no burning and stinging or pruritus for 32 minutes (duration of study) following topical application.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

All documents and other information sources cited herein are hereby incorporated in their entirety by reference.

The invention claimed is:
1. A composition comprising:
   i) 0.075-20% by weight of a capsaicinoid,
   ii) an extended release agent to slow the release of said capsaicinoid from said composition upon administration of said composition to a mammal, and
   iii) a surfactant,
   wherein said composition reduces or eliminates the burning and stinging created by said capsaicinoid upon topical administration.

* * * * *